(12) United States Patent
Lindsay et al.

(10) Patent No.: US 11,808,755 B2
(45) Date of Patent: Nov. 7, 2023

(54) DEVICE, SYSTEM AND METHOD FOR DIRECT ELECTRICAL MEASUREMENT OF ENZYME ACTIVITY

(71) Applicant: RECOGNITION ANALYTIX, INC., Phoenix, AZ (US)

(72) Inventors: Stuart Lindsay, Phoenix, AZ (US); Peiming Zhang, Phoenix, AZ (US)

(73) Assignee: RECOGNITION ANALYTIX, INC., Phoenix, AZ (US)

(*) Notice: Subject to any disclaimer, the term of this patent is extended or adjusted under 35 U.S.C. 154(b) by 22 days.

(21) Appl. No.: 17/055,771

(22) PCT Filed: May 16, 2019

(86) PCT No.: PCT/US2019/032707
§ 371 (c)(1),
(2) Date: Nov. 16, 2020

(87) PCT Pub. No.: WO2019/222527
PCT Pub. Date: Nov. 21, 2019

(65) Prior Publication Data
US 2021/0208127 A1 Jul. 8, 2021

Related U.S. Application Data

(60) Provisional application No. 62/812,312, filed on Mar. 1, 2019, provisional application No. 62/682,991, filed
(Continued)

(51) Int. Cl.
*G01N 33/487* (2006.01)
*C12Q 1/00* (2006.01)
*G01N 27/414* (2006.01)

(52) U.S. Cl.
CPC ....... *G01N 33/48721* (2013.01); *C12Q 1/005* (2013.01); *G01N 27/4146* (2013.01)

(58) Field of Classification Search
CPC ............ G01N 33/48721; C12Q 1/005
See application file for complete search history.

(56) References Cited

U.S. PATENT DOCUMENTS 5,198,543 A * 3/1993 Blanco ............... C12Q 1/6844
435/6.1
6,824,974 B2 11/2004 Pisharody et al.
(Continued)

FOREIGN PATENT DOCUMENTS

CN 104359946 A 2/2015
JP 2016188794 A 11/2016
(Continued)

OTHER PUBLICATIONS

M. Seifert, Characterization of Streptavidin Binding to Biotinylated, Binary Self-Assembled Thio Monolayers—Influence of Component Ratio and Solvent, Langmuir, 2010, 26(9), p. 6386-93. (Year: 2010).*

(Continued)

*Primary Examiner* — Caitlyn Mingyun Sun
(74) *Attorney, Agent, or Firm* — Casimir Jones, S.C.; Peter J. Schlueter

(57) ABSTRACT

The present disclosure relates to a device, system and method for sensing functional motions of a single protein molecule via direct attachment of one or more electrodes to the molecule. The present disclosure also relates to an array, a system comprising an array and method for sequencing a biopolymer using an array.

23 Claims, 18 Drawing Sheets

Specification includes a Sequence Listing.

Related U.S. Application Data on Jun. 10, 2018, provisional application No. 62/673,080, filed on May 17, 2018.

(56) References Cited

U.S. PATENT DOCUMENTS

| | | |
|---|---|---|
| 7,632,671 B2 | 12/2009 | Tong |
| 8,628,649 B2 | 1/2014 | Lindsay et al. |
| 8,961,757 B2 | 2/2015 | Nuckolls et al. |
| 8,968,540 B2 | 3/2015 | Reinhart et al. |
| 9,140,682 B2 | 9/2015 | Lindsay et al. |
| 9,274,430 B2 | 3/2016 | Gyarfas et al. |
| 9,376,713 B2 | 6/2016 | Bashir et al. |
| 9,593,372 B2 | 3/2017 | Lindsay et al. |
| 9,938,586 B2 | 4/2018 | Liang et al. |
| 10,379,102 B2 | 8/2019 | Lindsay et al. |
| 10,422,787 B2 | 9/2019 | Lindsay et al. |
| 10,508,296 B2 | 12/2019 | Merriman et al. |
| 10,913,966 B2 | 2/2021 | Merriman et al. |
| 2003/0124572 A1 | 7/2003 | Umek et al. |
| 2004/0146863 A1 | 7/2004 | Pisharody et al. |
| 2004/0249124 A1 | 12/2004 | Caruso et al. |
| 2009/0215156 A1 | 8/2009 | Chung et al. |
| 2009/0226899 A1 | 9/2009 | Chen |
| 2010/0084276 A1 | 4/2010 | Lindsay |
| 2010/0184062 A1 | 7/2010 | Steinmuller-Nethl et al. |
| 2010/0206731 A1 | 8/2010 | Lau et al. |
| 2010/0285514 A1 | 11/2010 | Claussen et al. |
| 2011/0098218 A1 | 4/2011 | Han et al. |
| 2011/0312529 A1 | 12/2011 | He et al. |
| 2012/0228386 A1 | 9/2012 | Wu et al. |
| 2013/0302901 A1 | 11/2013 | Lindsay et al. |
| 2014/0141525 A1 | 5/2014 | Albert et al. |
| 2015/0010935 A1 | 1/2015 | Lindsay et al. |
| 2015/0017655 A1 | 1/2015 | Huang et al. |
| 2015/0086994 A1 | 3/2015 | Williams et al. |
| 2015/0142327 A1 | 5/2015 | Ashcroft et al. |
| 2015/0144506 A1 | 5/2015 | Lindsay et al. |
| 2015/0285818 A1 | 10/2015 | Banala et al. |
| 2016/0018384 A1 | 1/2016 | Lindsay et al. |
| 2016/0025702 A1 | 1/2016 | Lindsay et al. |
| 2016/0083789 A1 | 3/2016 | Turner et al. |
| 2016/0097759 A1 | 4/2016 | Lindsay et al. |
| 2016/0108002 A1 | 4/2016 | Zhang et al. |
| 2016/0146828 A1 | 5/2016 | Lindsay et al. |
| 2016/0177383 A1 | 6/2016 | Ashcroft et al. |
| 2016/0194698 A1 | 7/2016 | Lindsay |
| 2016/0258925 A1 | 9/2016 | Gyarfas et al. |
| 2016/0280723 A1 | 9/2016 | Zhang et al. |
| 2016/0282295 A1 | 9/2016 | Wang et al. |
| 2016/0319343 A1 | 11/2016 | Korlach et al. |
| 2017/0003245 A1 | 1/2017 | Lindsay et al. |
| 2017/0016852 A1 | 1/2017 | Lindsay et al. |
| 2017/0037462 A1 | 2/2017 | Turner et al. |
| 2017/0038333 A1 | 2/2017 | Turner et al. |
| 2017/0038369 A1 | 2/2017 | Lindsay et al. |
| 2017/0044605 A1 | 2/2017 | Merriman et al. |
| 2017/0067902 A1 | 3/2017 | Zhang et al. |
| 2017/0137389 A1 | 5/2017 | Zhang et al. |
| 2017/0168039 A1 | 6/2017 | Lindsay et al. |
| 2018/0031549 A1 | 2/2018 | Chen et al. |
| 2018/0073071 A1 | 3/2018 | Ju et al. |
| 2018/0095081 A1 | 4/2018 | Albert et al. |
| 2018/0120286 A1 | 5/2018 | Lindsay et al. |
| 2018/0180567 A1 | 6/2018 | Li et al. |
| 2018/0305727 A1 | 10/2018 | Merriman et al. |
| 2018/0340220 A1 | 11/2018 | Merriman et al. |
| 2019/0094175 A1 | 3/2019 | Merriman et al. |
| 2019/0112643 A1 | 4/2019 | Aran et al. |
| 2019/0234902 A1 | 8/2019 | Lima, Jr. et al. |
| 2019/0309008 A1 | 10/2019 | Ju et al. |
| 2019/0330695 A1 | 10/2019 | Guo et al. |
| 2021/0208127 A1 | 7/2021 | Lindsay et al. |

FOREIGN PATENT DOCUMENTS

| | | | |
|---|---|---|---|
| WO | WO 2013/038272 | 3/2013 | |
| WO | 2014074727 A1 | 5/2014 | |
| WO | WO 2015/130781 | 9/2015 | |
| WO | WO 2015/131073 | 9/2015 | |
| WO | WO 2015/161119 | 10/2015 | |
| WO | WO 2015/170784 A1 | 11/2015 | |
| WO | 2016161402 A1 | 10/2016 | |
| WO | 2016210386 | 12/2016 | |
| WO | WO 2017/084998 | 5/2017 | |
| WO | WO-2017123416 A1 * | 7/2017 | ............ B82Y 15/00 |
| WO | 2017189930 A1 | 11/2017 | |
| WO | WO 2018/026855 | 2/2018 | |
| WO | WO 2019/086305 | 5/2019 | |
| WO | WO 2019/211622 | 11/2019 | |
| WO | WO 2019/217600 A1 | 11/2019 | |
| WO | WO 2019/222527 | 11/2019 | |
| WO | WO 2020/160300 | 8/2020 | |
| WO | WO 2020/257654 | 12/2020 | |
| WO | WO 2021/163275 | 8/2021 | |
| WO | WO 2021/173681 | 9/2021 | |
| WO | WO 2021/222791 | 11/2021 | |

OTHER PUBLICATIONS

C. Kotlowski, Fine discrimination of volatile compounds by graphene-immobilized odorant-binding proteins, Sensors and Actuators B: Chemical, 2018(256), p. 564-72. (Year: 2018).*

Chen, Y.-S., et al., "DNA sequencing using electrical conductance measurements of a DNA polymerase," Nature Nanotechnology, May 5, 2013, pp. 1-7; https://doi.org/10.1038/nnano.2013.71.

Choi, Y. et al., "Single-Molecule Lysozyme Dynamics Monitored by an Electronic Circuit," Science (2012) 335:319-324; DOI: 10.1126/science.1214824.

Olsen, T.J. et al., "Electronic Measurements of Single-Molecule Processing by DNA Polymerase I (Klenow Fragment)," Journal of the American Chemical Society (Apr. 30, 2013); pp. 1-12; DOI: 10.1021/ja311603r.

Zhang, B. et al., "Observation of giant conductance fluctuations in a protein," Nano Futures (2017) 1:1-15; https://doi.org/10.1088/2399-1984/aa8f91.

Ackerman et al., Massively multiplexed nucleic acid detection with Cas13. Nature. Jun. 2020;582(7811):277-282.

Adhikari et al., Conductivity of individual Geobacter pili. RSC Advances, 2016. 6: p. 8354-8357.

Alloway et al., Interface Dipoles Arising from Self-Assembled Monolayers on Gold: UV-Photoemission Studies of Alkanethiols and Partially Fluorinated Alkanethiols. J. Phys. Chem. B 2003, 107:11690-11699.

Altschul et al., Basic local alignment search tool. J Mol Biol. Oct. 5, 1990;215(3):403-10.

Altschul et al., Gapped BLAST and PSI-BLAST: a new generation of protein database search programs. Nucleic Acids Res. Sep. 1, 1997;25(17):3389-402.

Amdursky et al., Electronic transport via proteins. Adv Mater. Nov. 12, 2014;26(42):7142-61.

Amdursky et al., Solid-state electron transport via cytochrome c depends on electronic coupling to electrodes and across the protein. PNAS, Apr. 15, 2014, vol. 111, No. 15, pp. 5556-5561.

Artes et al., Transistor-like Behavior of Single Metalloprotein Junctions. Nano Lett.,2012, 12(6), pp. 2679-2684 (publication date (Web): Oct. 5, 2011).

Aubert et al., Intraprotein radical transfer during photoactivation of DNA photolyase. Nature. Jun. 1, 2000;405(6786):586-90.

Ausubel et al. Current Protocols in Molecular Biology, John Wiley & Sons, New York, 1998.

Bostick et al., Protein bioelectronics: a review of what we do and do not know. Rep Prog Phys. Feb. 2018;81(2):026601. 58 pages.

Chang et al., Chemical recognition and binding kinetics in a functionalized tunnel junction. Nanotechnology. Jun. 15, 2012;23(23):235101. 28 pages.

Chichil et al., Linkers in the structural biology of protein-protein interactions. Protein Sci. Feb. 2013;22(2):153-67.

(56) References Cited

OTHER PUBLICATIONS

Chin et al., Addition of p-Azido-l-phenylalanine to the Genetic Code of *Escherichia coli*. J. Am. Chem. Soc. 2002. 124,31, 9026-9027.
Choi et al. "Site-specific inhibition of integrin alpha v beta 3-vitronectin association by a serasp-val sequence through an Arg-Gly-Asp-binding site of the integrin." Proteomics, vol. 10,Issue 1, No. 1 Jan. 2010, pp. 72-80 (First published Oct. 30, 2009).
Cui et al., Reproducible measurement of single-molecule conductivity. Science. Oct. 19, 2001;294(5542):571-4.
Dellafiore et al., Modified Nucleoside Triphosphates for In-vitro Selection Techniques. Front Chem. May 4, 2016;4:18.
Duffy et al., Modified nucleic acids: replication, evolution, and next-generation therapeutics. BMC Biology, Sep. 2, 2020. 18:112. 14 pages.
Extended European Search Report for PCT/US2019031394, dated Jan. 5, 2022. 7 pages.
Fairhead et al., Plug-and-play pairing via defined divalent streptavidins. J Mol Biol. Jan. 9, 2014;426(1):199-214.
Fujino et al, Chimeric RNA Oligonucleotides Incorporating Triazole-Linked Trinucleotides: Synthesis and Function as mRNA in Cell-Free Translation Reactions. J Org Chem. Oct. 7, 2016;81(19):8967-8976.
Fulton et al., Purification of monoclonal antibody against Ebola GP1 protein expressed in Nicotiana benthamiana. J Chromatogr A. Apr. 10, 2015;1389:128-32.
Garg et al., Interface Electrostatics Dictates the Electron Transport via Bioelectronic Junctions. ACS Appl Mater Interfaces. Dec. 5, 2018;10(48):41599-41607.
Giese et al., Direct observation of hole transfer through DNA by hopping between adenine bases and by tunnelling. Nature. Jul. 19, 2001;412(6844):318-20.
Giese et al., Long distance charge transport through DNA: quantification and extension of the hopping model. Chemphyschem. Dec. 15, 2000;1(4):195-8.
Gonnet et al., Exhaustive matching of the entire protein sequence database. Science. Jun. 5, 1992;256(5062):1443-5.
Guo et al., Tuning electronic transport via hepta-alanine peptides junction by tryptophan doping. Proc Natl Acad Sci U S A. Sep. 27, 2016;113(39):10785-90.
Hajian et al., Detection of unamplified target genes via CRISPR-Cas9 immobilized on a graphene field-effect transistor. Nat Biomed Eng. Jun. 2019;3(6):427-437.
Harriman. Further comments on the redox potentials of tryptophan and tyrosine. Journal of Physical Chemisty 1987. 91:6102-6104.
Hohl et al. Engineering a Polyspecific Pyrrolysyl-tRNA Synthetase by a High Throughput FACS Screen. Sci Rep. Aug. 19, 2019;9(1):11971.
International Search Report and Written Opinion for PCT/US19/31394, dated Sep. 10, 2019. 11 pages.
International Search Report and Written Opinion for PCT/US20/15931, dated Jul. 27, 2020. 17 pages.
International Search Report and Written Opinion for PCT/US20/38740, dated Oct. 2, 2020. 14 pages.
International Search Report and Written Opinion for PCT/US21/17583, dated May 3, 2021. 9 pages.
International Search Report and Written Opinion for PCT/US21/19428, dated May 6, 2021. 25 pages.
International Search Report and Written Opinion for PCT/US21/27650, dated Aug. 25, 2021. 9 pages.
International Search Report and Written Opinion for PCT/US21/30239, dated Sep. 27, 2021. 10 pages.
International Search Report and Written Opinion for PCT/US21/34698, dated Sep. 30, 2021. 10 pages.
International Search Report and Written Opinion for PCT/US21/63851, dated Feb. 17, 2022. 9 pages.
International Search Report and Written Opinion for PCT/US21/65905, dated Mar. 17, 2022. 9 pages.
Jeffrey, An Introduction to Hydrogen Bonding. Oxford University Press New York. 1997. TOC only. 6 pages.
Kluenker et al., Monitoring Thiol-Ligand exchange on Au nanoparticle surfaces. Langmuir. Jan. 30, 2018;34(4):1700-1710.
Kyte et al., A simple method for displaying the hydropathic character of a protein. J Mol Biol. May 5, 1982;157(1):105-32.
Lagunas et al., Long distance electron transfer through the aqueous solution between redox partner proteins. Nat Commun. Dec. 4, 2019;9(1):5157.
Lai et al., Monoclonal antibody produced in plants efficiently treats West Nile virus infection in mice. Proc Natl Acad Sci U S A. Feb. 9, 2010;107(6):2419-24.
Lai et al., Robust production of virus-like particles and monoclonal antibodies with geminviral replicon vectors in lettuce. Plant Biotechnol J. Jan. 2012;10(1):95-104.
Leary et al., Unambiguous one-molecule conductance measurements under ambient conditions. Nano Lett. Jun. 8, 2011;11(6):2236-41.
Li et al., CRISPR-SE: a brute force search engine for CRISPR design. NAR Genom Bioinform. Feb. 23, 2021;3(1):Iqabo013.
Li et al., Synthesis and Photovoltaic effect on electron-withdrawing units for low band gap conjungated polymers bearing bi(thienylenevinylene) side chains. Polymers. 2019, vol. 11 iss 9 pp. 1-13.
Lindsay. Ubiquitous Electron Transport in Non-Electron Transfer Proteins. Life (Basel). May 20, 2020;10(5):72. 13 pages.
Liu et al., Vertical T cellimmunodomincance and epitope entropy determine HIV-1 escape. J Clin Invest. Jan. 2013;123(1):380-93.
Main et al., Design of stable alpha-helical arrays from an idealized TPR motif. Structure. May 2003;11(5):497-508.
Malvankar et al., Tunable metallic-like conductivity in microbial nanowire networks. Nat Nanotechnol. Aug. 7, 2011;6(9);573-9.
Marakova et al., An updated evolutionary classification of CRISPR-Cas systems. Nat Rev Microbiol. Nov. 2015;13(11):722-36.
Mckenzie et al., Recent progress in non-native nucleic acid modifications. Chem Soc Rev. Apr. 26, 2021;50(8):5126-5164.
Mejias et al., Controlled nanometric fibers of self-assembled designed protein scaffolds. Nanoscale. Oct. 7, 2014;6(19):10982-8.
Metsky et al., Diagnostic design with machine learning model-based optimization. bioRxiv 2020.11.28.401877: 95 pages.
Mullegama et al., Nucleic Acid Extraction from Human Biological Samples. Methods Mol Biol 2019;1897:359-383.
Nitzan. Chemical dynamics in condensed phases. Oxford University Press., Oxford. 2006. TOC only. 13 pages.
Odella et al., Controlling Proton-Coupled Electron Transfer in Bioinspired Artificial Photosynthetic Relays. J Am Chem Soc. Nov. 14, 2018;140(45):15450-15460.
Pang et al. "Fixed-Gap Tunnel Junction for Reading DNA Nucleotides" ACS Nano, 2014, 8(12), pp. 11994-12003 (Publication Date (Web): Nov. 7, 2014).
Pearson. Using the FASTA program to search protein and DNA sequence databases. Methods Mol Biol. 1994;24:307-31.
Quast et al., Cotranslational incorporation of non-strandard amino acids using cell-free protein synthesis. FEBS Lett. Jul. 8, 2015;589(15):1703-12.
Ruiz et al., Bioengineering a Single-Protein Junction. J Am Chem Soc. Nov. 1, 2017;139(43):15337-15346.
Sambrook et al., Molecular Cloning: A Laboratory Manual, 3d ed., Cold Spring Harbor Press, 2001. TOC only. 23 pages.
Sano et al., Cooperative biotin binding by streptavidin. Electrophorectic behavior and subunit association of streptavidin in the presence of 6 M urea. J Biol Chem. Feb. 25, 1990;265(6):3369-73.
Sek et al., Conductance of alpha-helical peptides trapped within molecular junctions. J Phys Chem B. Oct. 5, 2006;110(39):19671-7.
Sequences of amino acids as found on the world wide web at bmrb.wisc.edu/referenc/choufas. 4 pages.
Smith. The hydrophilic nature of a clean gold surface. J. Colloid Interface Science 1980. 75:51-55.
Staals et al., RNA targeting by the type III-A CRISPR-Cas Csm complex of Themus thermophilus. Mol Cell. Nov. 20, 2014;56(4):518-30.
Tripkovic et al., Standard hydrogen electrode and potential of zero charge in density functional calculations. Phys. Rev. B 2011. 84:115452.

(56) References Cited

OTHER PUBLICATIONS

Tuchband et al., Insulated gold scanning tunneling microscopy probes for recognition tunneling in an aqueous environment. Rev Sci Instrum. Jan. 2012;83(1):015102.

Vaish et al., A novel, modification-dependent ATP-binding aptamer selected from an RNA library incorporating a cationic functionality. Biochemistry. Jul. 29, 2003;42(29):8842-51.

Vattay et al., Quantum Criticality at the Origin of Life. Journal of Physics: Conference Series 2015. 626: p. 012023. 11 pages.

Willner et al., Mediated electron transfer in glutathione reductase organized in self-assembled monolayers on Au electrodes. J. Am. Chem. Soc., 1992. 114: p. 10965-10966.

Xiao et al., Conductance titration of single-peptide molecules. J Am Chem Soc. May 5, 2004;126(17):5370-1.

Yang et al., Plant-produced Zika virus envelope protein elicits neutralizing immune responses that correlate with protective immunity against Zika virus in mice. Plant Biotechnol J. Feb. 2018;16(2):572-580.

Zhang et al., Engineering an Enzyme for Direct Electrical Monitoring of Activity. ACS Nano. Feb. 25, 2020;14(2):1360-1368.

Zhang et al., Electronic Conductance Resonance in Non-Redox-Active Proteins. J Am Chem Soc. Apr. 1, 2020;142(13):6432-6438.

Zhang et al., Electronic Decay Length in a Protein Molucule. Nano Lett. Jun. 12, 2019;19(6):4017-4022.

Zhang et al., Role of contacts in long-range protein conductance. Proc Natl Acad Sci U S A. Mar. 26, 2019;116(13):5886-5891.

Zwolak et al. "Electronic Signature of DNA Nucleotides via Transverse Transport" NanoLett., 2005, 5(3), pp. 421-424 (Publication Date (Web): Feb. 12, 2005).

Anzai et al., "Avidin-biotin complexation for enzyme sensor applications" Trends in Analytical Chemistry, 1994, 13(5): 131-133.

Barhoumi et al: "Urease immobilization on biotinylated polypyrrole coated ChemFEC devices for urea biosensor development" IRBM, Apr. 1, 2008, 29(2-3): 192-201.

Cui et al: "Layer-by-layer 1 assembly of multilayer filme composed of avidin and biotin-labeled antibody for immunosensing", Biosensors And Bioelectronics, Jan. 1, 2003, 18(1): 59-67.

Ihalainene et al., "Application of paper-supported printed gold electrodes for impedimetric immunosensor development" Biosensors 2013, 3:1-17.

International Search Report and Written Opinion for PCT/US2022/032211, dated Sep. 29, 2022. 31 pages.

Ouerghi et al., "Impedimetric immunosensor using avidin-biotin for antibody immobilization" Bioelectrochemistry, May 15, 2002, 56(1-2): 131-133.

Prodromids et al., "Impedimetric immunosensors—A review" Electrochimica Acta, May 30, 2010, 55(14): 4227-4233.

Seifert, Characterization of Streptavidin Binding to Biotinylated, Binary Self-Assembled Thio Monolayers—Influence of Component Ratio and Solvent, Langmuir, 2010, 26(9): 6386-93.

Shimura & Yoshida, "Heterogeneous photocatalytic hydrogen production from water and biomass derivatives" Energy Environmental Science 2011, 4: 2467.

* cited by examiner

DEVICE, SYSTEM AND METHOD FOR DIRECT ELECTRICAL MEASUREMENT OF ENZYME ACTIVITY

FEDERALLY SPONSORED RESEARCH OR DEVELOPMENT

This invention was made with government support under HG910080 awarded by the National Institutes of Health. The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 3,054 Byte ASCII (Text) file named "2020-11-16_38875-254_SQL.txt," created on Nov. 16, 2020.

BACKGROUND

Electrical readout of motions that underlie functions of a native protein might enable many new types of analytical measurement without labeling. For example, monitoring functional fluctuations of an enzyme would provide a rapid and simple way of screening candidate drug molecules. Monitoring the fluctuations of proteins that process biopolymers would reveal information about their composition and conformation.

Electrical readout of enzyme function was demonstrated by Choi et al. (Choi, Moody et al. 2012) who showed that telegraph noise, induced in a carbon nanotube field effect transistor, reflected the functional motion of the enzyme lysozyme when acting on its substrate, peptidoglycan. It was realized that monitoring the fluctuations of precessive enzymes, such as DNA polymerase might thus give a method for sequencing DNA. One example was given In a controversial paper, in which the Huang group (Chen, Lee et al. 2013) claimed to measure electrical fluctuations in a polymerase as nucleotides were incorporated into an extending chain, the signals reporting the sequence of the template being extended with high accuracy. The paper was subsequently retracted (*Nature Nanotechnology* 8, 452-458 (2013); published online 5 May 2013; corrected after print 11 Jul. 2013 and 28 Aug. 2013; retracted after print 3 Jun. 2015) but illustrates what might be possible if the structural fluctuations of a protein could be monitored by an electrical readout. More significantly, a working realization of this proposal was demonstrated around the same time by the Collins group who used a carbon nanotube field effect transistor to which a polymerase was tethered (Olsen, Choi et al. 2013). The signals consisted of telegraph noise that were shown to be associated with the opening and closing of the polymerase as nucleotides were incorporated. Importantly, the characteristics of the noise reflected the specific nucleotide that was being incorporated, opening the way to electrical single-molecule readout of DNA sequences.

In Olsen, Choi et al. 2013, fluctuations of the protein were detected indirectly via the electric field fluctuations they generate, the field fluctuations being sensed by a field effect transistor channel in close proximity to the polymerase or lysozyme. FIG. 1 illustrates the proposal of Chen et al. A polymerase 1 bound with a primed DNA template 2 in the presence of nucleotide triphosphates in solution 3 is bound by means of antibodies 4 to gold beads 5 that span the gap between the source 6 and drain 7 of a field effect transistor, the channel of which 8 is formed over a gate electrode 9. In view of the retraction of the original report, it is not clear that this invention actually worked, but it contains many of the elements of the successful invention of the Collins group. This is illustrated in FIG. 2A where the source 21 and drain 22 of a field effect transistor are joined by a carbon nanotube 23 that forms the channel of the transistor. An enzyme (lysozyme in this case) 24 is attached to the carbon nanotube. A semiconductor back-gate 25 is used to set the transistor to its most sensitive operating point, midway between turn-on and turn off, and enzyme activity is detected via fluctuations in the FET current. In a later paper, the same group showed (FIG. 2B) how a polymerase 26 attached to the carbon nanotube channel 23 and bound by a primed DNA template 27 generated noise spikes, each one of which was associated with the incorporation of a nucleotide by the polymerase. Two examples of the train of signals obtained are given in FIG. 2C for a poly(dA) 28 and a poly(dC) 29. Clear differences in the signals show that sequencing is possible though the noise background 30 from the CNT FET is significant compared to the signal level 31. A rather similar method has been proposed by Merriman and Mola (Merriman and Mola, 2016). This is illustrated in FIG. 2C. A polymerase 436 is chemically linked via a linker 437 to a molecular wire 433 that is connected to the source 438 and drain 439 of a field effect transistor. A gate electrode 440 is placed below the molecular wire. The data presented in their patent application seems to indicate even lower signal levels than those obtained in the device of Olsen et al.

Clearly, it would be desirable to make a more direct electrical connection to the enzyme under test. We have developed a technology called recognition tunneling and have used recognition molecules to bind a protein to at least one of a pair of closely spaced electrodes (Zhang, Song et al. 2017). This approach is illustrated in FIG. 3. The device consists of a first electrode 41 and a second electrode 42 separated by a thin dielectric layer 43. Recognition molecules 44 are strongly attached to each of the electrodes by, for example, thiol-metal bonds. The molecules are chosen to be specifically recognized and bound by a target protein 45. These recognition events are generally reversible, and so unsuitable for holding a protein of interest in the gap for studies of its function. Thus, our previous technology of recognition tunneling is inapplicable to the present problem and irrelevant to it, as here we need to keep a known protein connected to the measuring device, rather than use the measuring device to detect the arrival of an unknown protein. More limiting still, is the requirement that these devices be operated at a high enough bias ($V_t$, 46) such that the bias itself drives the protein into a mode where telegraph noise fluctuations in current (47) are generated. In the case of this published work, where the protein was integrin and the recognition molecule was an RGD peptide, protein binding is detected by operating the device at a relatively high bias (>100 mV) and observing the fluctuations induced by the applied bias. The use of voltage-induced fluctuations as a detector of protein binding entirely precludes the use of this device to measure fluctuations in a protein's structure and conformation that enable the protein's critical biomolecular function, because these voltage-induced fluctuations occur in all proteins exposed to a high enough potential difference, regardless of functional motions. Therefore, in the art previously discussed, signals from these critical functional motions cannot be distinguished from voltage-induced fluctuations. Accordingly, it is desired to find a system and method for detecting the binding of a protein molecule across a pair of electrodes in conditions that eliminate voltage-induced conductance fluctuations and keep the protein in place while it is exposed to chemical stimuli that generate key and measurable functional fluctuations and to measure the response of those fluctuations to other chemicals, such as candidate drugs or biopolymers.

Citation of any reference in this section is not to be construed as an admission that such reference is prior art to the present disclosure.

SUMMARY

The present disclosure relates to devices, systems and methods for direct electrical measurement of protein activity. In some embodiments, a device is provided, the device comprising: a first and a second electrode, the first and second electrode being separated by a gap; a protein attached to one or both electrodes; wherein the first electrode and the second electrode are configured for contact with a sample to be analyzed.

In some embodiments, the protein is attached to one electrode. In other embodiments, the protein is attached to two electrodes.

In some embodiments, the device further comprises an insulating dielectric layer disposed within the gap.

In some embodiments, the protein is selected from the group consisting of a polymerase, a nuclease, a proteasome, a glycopeptidase, a glycosidase, a kinase, and an endonuclease.

In some embodiments, the protein is attached to one electrode. In other embodiments, the protein is attached to both electrodes.

In some embodiments, the protein is attached to the electrode via a linker.

In some embodiments, the device comprises: a first and a second electrode, the first and second electrode being separated by a gap; a protein attached to one or both electrodes; wherein a current fluctuation is produced when the protein interacts with a chemical entity.

In some embodiments, a device is provided, the device comprising:
(a) a dielectric substrate;
(b) a first electrode disposed on the dielectric substrate;
(c) an insulating dielectric layer disposed on the first electrode;
(d) a second electrode disposed on the insulating dielectric layer;
(e) a passivation layer disposed on the second electrode;
(f) a protein attached to one or both the electrodes;
wherein the first electrode, the insulating dielectric layer, the second electrode and passivation layer have an opening formed therethrough.

In some embodiments, the device comprises: a first and a second electrode, the first and second electrode being separated by a gap; a protein attached to one or both electrodes; wherein the first electrode and the second electrode have an opening formed therethrough.

In some embodiments, the device comprises: a first and a second electrode, the first and second electrode being coplanar and separated by a gap; a protein attached to one or both electrodes; wherein the first electrode and the second electrodes are configured for contact with a sample to be analyzed.

In some embodiments, the device further comprises an insulating dielectric layer disposed within the gap.

In some embodiments, the protein is attached to one electrode. In some aspects of this embodiment, the protein is a polymerase. In some aspects of this embodiment, the polymerase is attached to the electrode via a linker. In some aspects, the polymerase is a biotinylated polymerase. In some aspects, the polymerase is a biotinylated polymerase and is attached to the electrode via streptavidin.

In some embodiments of the device, the first and/or second electrode comprise a metal selected from the group consisting of gold, platinum, palladium, and ruthenium. In some embodiments, the metal is palladium.

In some embodiments, the gap has a width of about 1.0 nm to about 20.0 nm. In some embodiments, the gap has a width of about 1.0 nm to about 10.0 nm. In some embodiments, the gap has a width of about 2.0 nm to about 10.0 nm. In some embodiments, the gap has a width of about 1.0 nm to about 7.5 nm. In some embodiments, the gap has a width of about 1.0 nm to about 5.0 nm. In some embodiments, the gap has a width of about 4.0 nm to about 5.0 nm. In some embodiments, the gap has a width of about 5.0 nm to about 6.0 nm.

In some embodiments, the device can be used to detect a single molecule.

In some embodiments, a system is provided, the system comprising a device as described herein; a means for introducing a chemical entity that is capable of interacting with the protein; a means for applying a bias between the first and second electrode of value; and a means for monitoring fluctuations that occur as a chemical entity interacts with the protein.

In some embodiments, the bias is between 1 mV and 50 mV.

In some embodiments, the bias is between 1 mV and 100 mV.

In some embodiments, a method is provided, the method comprising (a) providing a system as described herein; (b) contacting the protein with a chemical entity; (c) applying a bias between the first and second electrode of value such that spontaneous fluctuations of the current between the electrodes do not occur; (d) detecting fluctuations that occur as the chemical entity interacts with the protein.

The methods of the disclosure can be used to detect the activity of a single protein molecule. The methods can also be used to sequence a biopolymer. The methods can also be used in drug screening assays. Advantageously, the methods require no labels or special chemistries.

The methods of sequencing a biopolymer provide for long reads (>10 kB), and polymerase runs at the speed of native polymerase (100 nt/s).

The devices of the disclosure have simple device geometries, which allows for easy scale up.

The present disclosure relates to an array, system and method for sequencing a biopolymer by direct electrical measurements on single processive protein.

In one embodiment, the present disclosure provides an array for sequencing a biopolymer comprising: an arrangement of a plurality of devices, as described herein. In one aspect of this embodiment, the array is for sequencing DNA.

The present disclosure provides a system for direct measurement of protein activity. The system comprises: (a) an array as described herein; (b) optionally a means for introducing and removing a solution to the array; (c) a means for applying a bias between the first and second electrode; and (d) a means for monitoring the current generated between the first and second electrodes. In one aspect of this embodiment, the system is for direct measurement of polymerase activity.

The present disclosure also provides a method for sequencing a biopolymer. In one embodiment, the method is for sequencing DNA, the method comprises: (a) introducing a solution comprising a DNA template to a system as described herein; (b) measuring a first current generated when a bias is applied to a system as described herein; (b) introducing a solution comprising a dNTP to the system under conditions that allow for incorporation of the dNTP complementary to the DNA template; (c) measuring a second current generated in step (b); (d) removing the solution comprising unincorporated dNTP; (e) repeating steps (b) through (d) with each of the remaining three types of dNTPs not used in step (b); (f) repeating steps (b) through (e); wherein the DNA is sequenced from the generated current signals.

In another embodiment, the method comprises: (a) introducing a solution comprising a DNA template to a system as described herein; (b) measuring a first current generated when a bias is applied to a system as described herein; (b) introducing a solution comprising at least two types of dNTPs to the system under conditions that allow for incorporation of the dNTP complementary to the DNA template, wherein the types of dNTPs are present in the solution at different concentrations; (c) measuring a second current generated in step (b); (d) removing the solution comprising the unincorporated dNTPs; (e) repeating steps (b) through (d) with the remaining types of dNTPs not used in step (b); (f) repeating steps (b) through (e); wherein the DNA is sequenced from the generated current signals.

DETAILED DESCRIPTION

Figure 1:
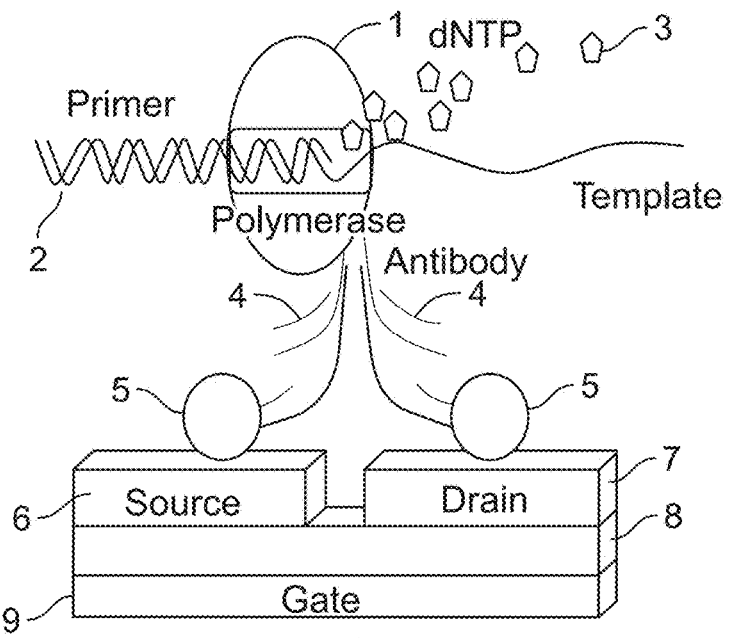
FIG. 1 shows a known detection system for polymerase fluctuations according to Chen et al.

The disclosure includes at least the following:
(1.) A device substantially as shown and described.
(2.) A system for direct electrical measurement of protein activity as shown and described.
(3.) A method for detecting protein activity as shown and described.
(4.) A method of sequencing a biopolymer as shown and described.

(5.) A device for direct measurement of protein activity, the device comprising a first and a second electrode, the first and second electrode being separated by a gap; and a protein attached to one or both electrodes; wherein the first electrode and the second electrode have an opening formed therethrough.

(6.) The device of the above (5.), wherein the gap has a width of about 1.0 nm to about 20.0 nm.

(7.) A device for direct measurement of protein activity, the device comprising:
   (a) a dielectric substrate;
   (b) a first electrode disposed on the dielectric substrate;
   (c) an insulating dielectric layer disposed on the first electrode;
   (d) a second electrode disposed on the insulating dielectric layer;
   (e) a passivation layer disposed on the second electrode;
   (f) a protein attached to one or both the electrodes;
wherein the first electrode, the insulating dielectric layer, the second electrode and passivation layer have an opening formed therethrough.

(8.) A device for direct measurement of protein activity, the device comprising:
   (a) a first and a second electrode, the first and second electrode being co-planar and separated by a gap;
   (b) a protein attached to at least one electrode;
wherein the first electrode and the second electrodes are configured for contact with a sample to be analyzed.

(9.) The device of any of the above (5.) to (8.), wherein the protein is selected from the group consisting of a polymerase, a nuclease, a proteasome, a glycopeptidase, a glycosidase, a kinase and an endonuclease.

(10.) The device of the above (9.), wherein the protein is a polymerase.

(11.) The device of the above (10.), wherein the polymerase is attached to one electrode.

(12.) The device of the above (10.) or (11.), wherein the polymerase is attached to the electrode via a linker.

(13.) The device of the any of the above (10.) to (12.), wherein the protein is a biotinylated polymerase.

(14.) The device of the above (13.), wherein the biotinylated polymerase is attached to the electrode via a thio-streptavidin linker.

(15.) The device of the any of the above (5.) to (14.), wherein the first and/or second electrode comprise a metal selected from the group consisting of gold, platinum, palladium, and ruthenium.

(16.) The device of the above (15.), wherein the first and/or second electrode comprise palladium.

(17.) A device for direct measurement of protein activity, the device comprising:
   (a) a dielectric substrate;
   (b) a first electrode disposed on the dielectric substrate;
   (c) a second electrode disposed on the dielectric substrate, wherein the first and second electrode being separated by a gap between 1 and 10 nm;
   (d) a passivation layer disposed on top of the electrodes; and
   (e) a protein attached to one or both the electrodes;
wherein the passivation layer has an opening formed therethrough positioned to allow a sample to pass to the gap between the first and second electrode.

(18.) A system for direct electrical measurement of protein activity comprising
   (a) a device of any of the above (5.) to (17.);
   (b) a means for introducing a chemical entity that is capable of interacting with the protein;
   (c) a means for applying a bias between the first and second electrode; and
   (d) a means for monitoring fluctuations that occur as the chemical entity interacts with the protein.

(19.) The system of the above (18.), wherein the protein is a polymerase.

(20.) The system of the above (18.), wherein the protein is an exonuclease, proteasome, or glycan.

(21.) The system of the above (18.), wherein the protein is a kinase.

(22.) A method of detecting the activity of a single protein molecule, the method comprising
   (a) introducing a chemical entity that is capable of interacting with the protein molecule to the system of the above (18.);
   (b) applying a bias between the two electrodes chosen so that a steady DC current is observed; and
   (c) observing fluctuations in current between the two electrodes that arise when the chemical entity interacts with the protein.

(23.) The method of the above (22.), wherein the protein is selected from the group consisting of a polymerase, a nuclease, a proteasome, a glycopeptidase, a glycosidase, a kinase and an endonuclease.

(24.) The method of the above (22.) or (23.), wherein the chemical entity is selected from the group consisting of a nucleotide triphosphate, a nucleic acid, a peptide, a glycan and a kinase.

(25.) A method of sequencing DNA, said method comprising
   (a) introducing a primed DNA template to the system of the above (18.);
   (b) introducing a solution comprising the four dNTPs;
   (c) applying a bias between the two electrodes chosen so that a steady DC current is observed;
   (d) detecting fluctuations in current between the two electrodes that arise when each new nucleotide is incorporated to the primer; and
   (e) determining the identity of each of nucleotides being incorporated.

(26.) The method of the above (25.), wherein the solution comprises the four dNTPs at about the same concentration relative to each other.

(27.) The method of the above (25.) or (26.), wherein the concentrations of the dNTPs are about equal to or above the saturation concentration of the template-bound polymerase.

(28.) The method of any of the above (25.) through (27.), wherein step (d) comprises detecting the presence of one or more current spike(s).

(29.) The method of any of the above (25.) through (27.), wherein step (e) comprises using the characteristics of each spike.

(30.) A method of sequencing a biopolymer, said method comprising
   (a) introducing a biopolymer to the system of the above (18.);
   (b) applying a bias between the two electrodes chosen so that a steady DC current is observed;
   (c) detecting fluctuations in current between the two electrodes that arise when a monomer is removed from the end of the biopolymer; and
   (d) determining the identity of each monomer removed from the biopolymer.

(31.) The method of the above (30.), wherein the biopolymer is DNA, a peptide, or a glycan.

(32.) A method of detecting the activity of kinase, the method comprising
(a) introducing a candidate kinase inhibitor molecule to the system of the above (20.);
(b) applying a bias between the two electrodes chosen so that a steady DC current is observed;
(c) detecting fluctuations in current between the two electrodes that arise when the kinase interacts with the candidate kinase inhibitor molecule; and
(d) determining whether the kinase has activity in the presence of the candidate kinase inhibitor molecule.

(33.) An array for sequencing a biopolymer as herein described.

(34.) An array for sequencing DNA as herein described.

(35.) An array for sequencing DNA comprising:
an arrangement of a plurality of devices, wherein each device comprises:
(a) a dielectric substrate;
(b) a first electrode disposed on the dielectric substrate;
(c) an insulating dielectric layer disposed on the first electrode;
(d) a second electrode disposed on the insulating dielectric layer;
(e) a passivation layer disposed on the second electrode; and
(f) a polymerase molecule attached to the first and second electrode,
wherein the first electrode, the insulating dielectric layer, the second electrode and passivation layer have an opening formed therethrough.

(36.) An array for sequencing DNA comprising:
an arrangement of a plurality of devices, wherein the device comprises:
(a) a dielectric substrate;
(b) a first electrode disposed on the dielectric substrate;
(c) a second electrode disposed on the dielectric substrate;
(d) a passivation layer disposed on top of the electrodes; and
(e) a polymerase molecule attached to one or both the electrodes;
wherein the passivation layer has an opening formed therethrough.

(37.) An array for sequencing DNA comprising:
an arrangement of a plurality of devices, wherein the device comprises:
(a) a first and a second electrode, the first and second electrode being separated by a gap and lying in a plane together with the second electrode;
(b) a polymerase attached to at least one electrode;
wherein the first electrode and the second electrodes are configured for contact with a sample to be analyzed.

(38.) The array of any of the above (33.) to (37.), wherein the arrangement is a grid.

(39.) A system for direct measurement of polymerase activity comprising:
(a) an array as described herein;
(b) optionally a means for introducing and removing a solution to the array;
(c) a means for applying a bias between the first and second electrode; and
(d) a means for monitoring the current generated between the first and second electrodes.

(40.) A method for sequencing DNA, the method comprising:
(a) introducing a solution comprising a DNA template to a system as described herein;
(b) measuring a first current generated when a bias is applied to a system as described herein;
(c) introducing a solution comprising a dNTP to the system under conditions that allow for incorporation of the dNTP complementary to the DNA template;
(d) measuring a second current generated in step (c);
(e) removing the solution comprising unincorporated dNTP;
(f) repeating steps (c) through (e) with each of the remaining three types of dNTPs not used in step (c); and
(g) repeating steps (c) through (f);
wherein the DNA is sequenced from the generated current signals.

(41.) A method for sequencing DNA, the method comprising:
(a) introducing a solution comprising a DNA template to a system as described herein;
(b) measuring a first current generated when a bias is applied to a system as described herein;
(c) introducing a solution comprising at least two types of dNTPs to the system under conditions that allow for incorporation of the dNTP complementary to the DNA template, wherein the types of dNTPs are present in the solution at different concentrations;
(d) measuring a second current generated in step (b);
(e) removing the solution comprising the unincorporated dNTPs;
(f) repeating steps (c) through (e) with the remaining types of dNTPs not used in step (c); and
(g) repeating steps (c) through (f);
wherein the DNA is sequenced from the generated current signals.

(42.) The method of the above (41.), wherein the solution in step (c) comprises four types of dNTPs.

(43.) The method of the above (41.), wherein the solution in step (c) comprises at least two types of dNTPs.

Definitions

Unless defined otherwise, all technical and scientific terms used herein have the same meaning as those commonly understood by one of ordinary skill in the art to which this invention belongs. Although methods and materials similar or equivalent to those described herein can be used in the practice or testing of the present disclosure, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The term "a" or "an" may mean more than one of an item.

The terms "and" and "or" may refer to either the conjunctive or disjunctive and mean "and/or".

The term "about" means within plus or minus 10% of a stated value. For example, "about 100" would refer to any number between 90 and 110.

The term "nucleotide" refers to a base-sugar-phosphate combination and includes ribonucleoside triphosphates ATP, UTP, CTG, GTP and deoxyribonucleoside triphosphates such as dATP, dCTP, dITP, dUTP, dGTP, dTTP, or derivatives thereof.

Device and System for Direct Measurement of Protein Activity

The present disclosure provides a device for direct measurement of protein activity. In one embodiment, the device comprises a first and a second electrode, the first and second electrode being separated by a gap; and a protein attached to one or both electrodes; wherein the first electrode and the second electrode have an opening formed therethrough.

In another embodiment, the device comprises a first and a second electrode, the first and second electrode being separated by a gap; and a protein attached to one or both electrodes.

In some embodiments, the device comprises:
(a) a dielectric substrate;
(b) a first electrode disposed on the dielectric substrate;
(c) an insulating dielectric layer disposed on the first electrode;
(d) a second electrode disposed on the insulating dielectric layer;
(e) a passivation layer disposed on the second electrode;
(f) a protein attached to one or both the electrodes;
wherein the first electrode, the insulating dielectric layer, the second electrode and passivation layer have an opening formed therethrough.

In some embodiments, the device comprises:
(a) a dielectric substrate;
(b) a first electrode disposed on the dielectric substrate;
(c) a second electrode disposed on the insulating dielectric layer;
(d) a passivation layer disposed on top of the electrodes; and
(e) a protein attached to one or both the electrodes;
wherein the passivation layer has an opening formed therethrough.

In some embodiments, the device comprises:
(a) a first and a second electrode, the first and second electrode being co-planar and separated by a gap and lying in a plane together with the second electrode;
(b) a protein attached to at least one electrode;
wherein the first electrode and the second electrodes are configured for contact with a sample to be analyzed.

In embodiments in which the electrodes are planar, the device advantageously does not require a dielectric layer. Devices requiring dielectric layers can suffer from drawbacks. Dielectric layers require adhesion layers to adhere to the electrodes. These adhesion layers can oxidize upon exposure to air, which, in effect, increases the size of the gap between the electrodes. To compensate for this effect, the dielectric layer can be made thinner. However, a thin dielectric layer is susceptible to pinholes, which can be difficult to eliminate.

In each of the device embodiments described herein, the protein is selected from the group consisting of a polymerase, a nuclease, a proteasome, a glycopeptidase, a glycosidase, a kinase and an endonuclease.

The protein can be attached to one electrode directly or indirectly. In some embodiments, the protein is attached to the electrode via a linker. In some embodiments, the protein is attached to the electrode indirectly via interactions with a ligand attached to the electrode. In some embodiments, the protein is modified to incorporate a ligand-binding site.

In one embodiment, the device comprises: a first and a second electrode, the first and second electrode being separated by a gap; a polymerase attached to one or both electrodes; wherein the first electrode and the second electrode have an opening formed therethrough.

In some embodiments, the polymerase is attached to one electrode. In some aspects of this embodiment, the polymerase is attached to the electrode via a linker. In some aspects, the polymerase is a biotinylated polymerase. In some aspects, the polymerase is a biotinylated polymerase and is attached to the electrode via streptavidin.

In each of the device embodiments described herein, the first and/or second electrode comprise a metal selected from the group consisting of gold, platinum, palladium, and ruthenium. In some embodiments, the metal is palladium.

In some embodiments, the gap has a width of about 1.0 nm to about 20.0 nm. In some embodiments, the gap has a width of about 1.0 nm to about 10.0 nm. In some embodiments, the gap has a width of about 1.0 nm to about 7.5 nm. In some embodiments, the gap has a width of about 1.0 nm to about 5.0 nm. In some embodiments, the gap has a width of about 4.0 nm to about 5.0 nm.

In some embodiments, the device can be used to detect a single molecule.

The present disclosure also provides a system for direct measurement of protein activity. The system comprises a device as described herein; a means for introducing a chemical entity that is capable of interacting with the protein; a means for applying a bias between the first and second electrode; and a means for monitoring the current generated between the first and second electrodes as the chemical entity interacts with the protein.

In each of the system embodiments described herein, the protein is selected from the group consisting of a polymerase, a nuclease, a proteasome, a glycopeptidase, a glycosidase, a kinase and an endonuclease. In one embodiment, the protein is a polymerase.

When the protein is a polymerase, the polymerase is attached to one electrode, or preferably both electrodes. In some aspects of this embodiment, the polymerase is attached to the electrodes via one or more linkers. In some aspects, the polymerase is a biotinylated polymerase. In some aspects, the polymerase is a biotinylated polymerase and is attached to the electrode via streptavidin.

In each of the system embodiments described herein, the first and/or second electrode comprise a metal selected from the group consisting of gold, platinum, palladium, and ruthenium. In some embodiments, the metal is palladium.

In some embodiments, the gap has a width of about 1.0 nm to about 20.0 nm. In some embodiments, the gap has a width of about 1.0 nm to about 10.0 nm. In some embodiments, the gap has a width of about 1.0 nm to about 7.5 nm. In some embodiments, the gap has a width of about 1.0 nm to about 5.0 nm. In some embodiments, the gap has a width of about 4.0 nm to about 5.0 nm.

Figure 4:
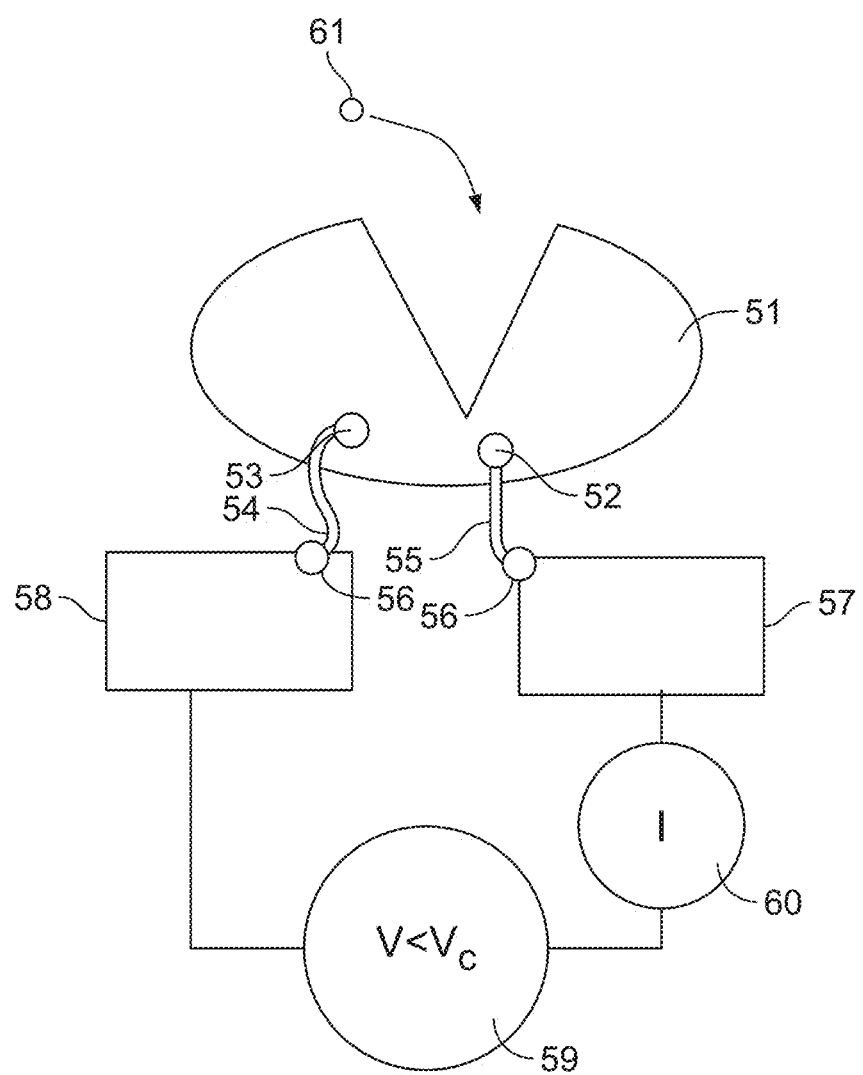
FIG. 4 shows a schematic diagram of an embodiment of the disclosure.

FIG. 4 shows a schematic diagram of a system according to an embodiment of the disclosure. A protein molecule 51 is covalently modified at certain sites 53 and 54. Such sites can be surface cysteine residues modified by reaction with a maleimide, lysine residues modified by means of an NHS ester or the insertion of a histidine tag at the N or C terminus of the protein to bind nitrilotriacetic acid, or by biotinylation of the protein and attachment via thiolated streptavidin molecules attached to the electrodes. Other means of attachment such as Myc tags or GST tags may be used as is well known in the art. The critical and unique design aspects of this embodiment are that the protein itself is utilized as the detector, to which end strong and permanent chemical tethers are used to attach the protein to the electrodes. The modified sites are coupled to flexible linkers, which may be short (1 to 10 repeats) alkane oligomers or polyethylene glycol oligomers or short peptide chains incorporated into the protein recombinantly. These are in turn terminated by reactive groups 56 that tether the linker molecules to the metal electrodes 57 and 58. While a variety of linkages are possible, thiol linkages are preferred, and amines may also be used, as can biotin-streptavidin linkages. A bias 59 is applied between the two electrodes and the current passing between the electrodes is monitored 60. The system is immersed in a buffer solution containing ions necessary for enzyme function and the effects of introducing chemical entity 61 (such as a substrate for the enzyme, and/or a drug) is recorded.

Figure 5A:
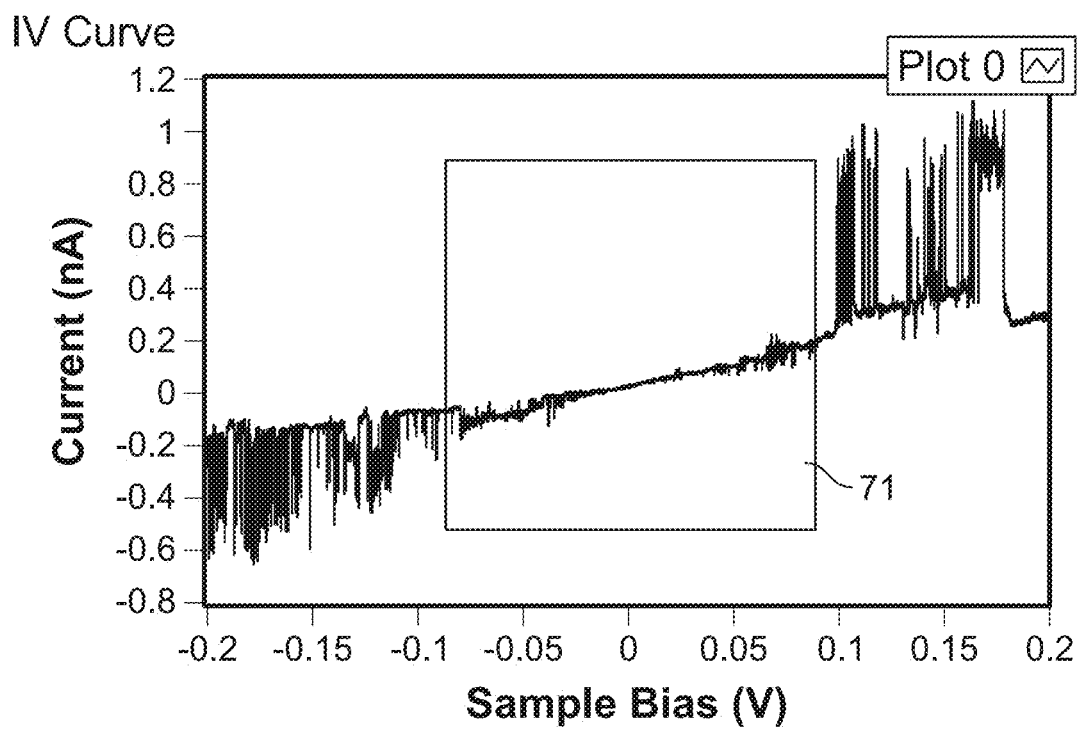
FIG. 5A shows the linear current voltage characteristic obtained when a protein is bound at two points as shown in FIG. 4.
Figure 5B:
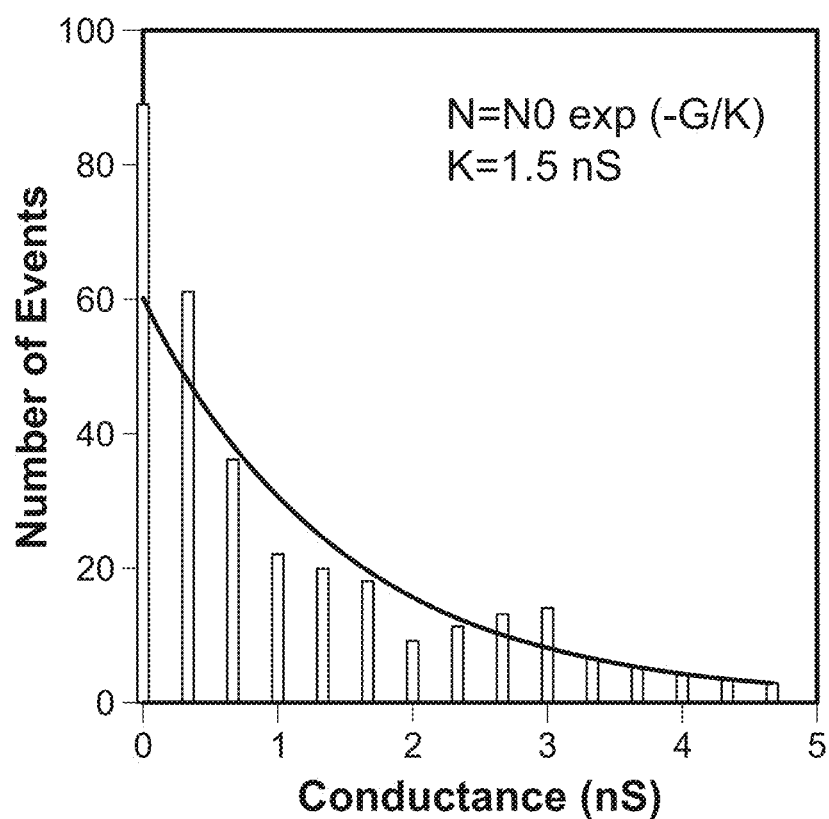
FIG. 5B shows the distribution of slopes of the linear region for a large number of single molecule measurements.

The basis of the present disclosure lies in a remarkably unexpected and very recent observation about the behavior of a protein in a large (approximately 4.5 nm) gap when the protein is strongly tethered to two electrodes as described above. We find that below the critical bias voltage previously reported for the onset of telegraph noise signals, a simple linear (Ohmic) response is found. This is completely unexpected because proteins are believed to be molecular solids in which the mode of electron transport should only be tunneling. However, tunneling cannot account for the large currents with linear current-voltages observed when proteins are tethered in the manner described in FIG. 4. An example of a typical current-voltage curve measured on a single protein molecule is shown in FIG. 5. Large noise fluctuations are observed above about ±100 mV as previously reported, but below ±100 mV (boxed area labeled 71 in FIG. 5A) there is a linear region which implies a remarkably high DC conductance for the protein, even over this large (4.5 nm) distance. When this linear region is fitted and a distribution of fitted conductances obtained, the conductance distribution can be fitted by an exponential distribution as shown in FIG. 5B (solid line is the fit). Note that in this case the mean conductance, K, has a value of 1.5 nS.

Figure 13:
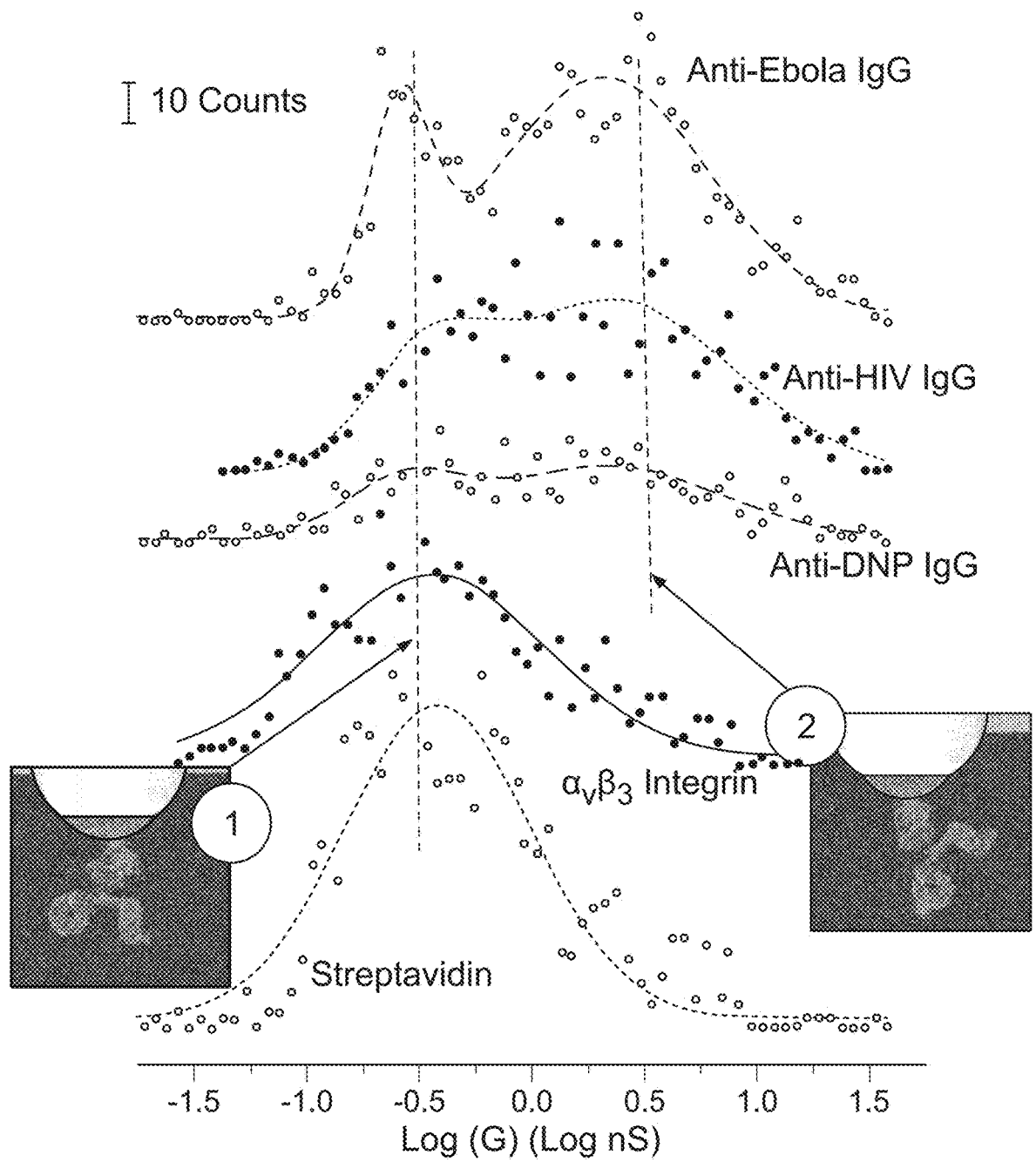
FIG. 13 shows distributions of measured conductances (log scale) for three antibodies and integrin bound to peptide ligands (as listed in Table 1) on Pd electrodes for a gap of about 4.5 nm, with the exception of the data for streptavidin coupled by thiol bonds to the electrodes where data was taken at a gap of about 2.5 nm. The distributions are arbitrarily displaced vertically for clarity. The insets illustrate how the antibodies, with two binding sites for peptide attached to the electrodes can bridge the gap, resulting the second, higher peak in conductance (labeled "2"). Single connections can also occur ("1"). These data show how high conductance (about 2 nS) can be obtained over long distances (the 13 nm between the binding sites of the antibodies) if two chemical connections are made between the protein and the electrodes, one to each electrode.

A larger collection of measurements reveals a more complex distribution of conductances as shown in FIG. 13. This figure plots histograms of the frequency of a given conductance versus conductance for a series of proteins coupled to the electrodes by various means. The conductance scale is logarithmic (base 10) and the peaks that are fitted as shown by the lines are Gaussian, so these conductances are distributed according to a log-normal distribution. (The distributions have been arbitrarily displaced vertically for clarity.) The proteins are tethered to the electrodes either by binding to a specific ligand for a particular protein, or, in the case of streptavidin via thiol linkages. The ligands were chemically attached to the electrodes vis thiol (cysteine) linkages. The various proteins, their ligands, the dissociation constant for the protein-ligand complex, controls used to verify specific binding and the peaks values of conductance obtained by fitting the distributions are listed in Table 1.

TABLE 1

Proteins used in the conductance study

| Protein | Ligand | $K_D$ | Control | Peak Conductance (nS) |
|---|---|---|---|---|
| IgE Anti-DNP | Thiolated-dinitrophenol | 65 nM | IgE isotype | 0.266, 1.95 |
| IgG Anti-HIV | CHNTPVYKLDISEATQV | 240 nM | IgG isotype | 0.334, 2.21 |
| IgG Anti-Ebola | CALDRWEKIRLR | 1400 nM | IgG isotype | 0.260, 2.09 |
| $\alpha v \beta_3$ Integrin | Cyclic RGD-C | ~10 nM | $\alpha_4 \beta_1$ Integrin | 0.341 |
| Thio-Streptavidin | NA | NA | Add Biotin | 0.336 |

No conductance was observed when electrodes were exposed to the control molecules listed, showing that specific chemical tethering of the protein to the electrodes is required for electronic conductance to be observed.

In the case of the three antibodies, two binding sites are available, one at each of the two binding domains, separated by 13 nm. As a consequence, a second, higher conductance peak is observed in the distributions for these three molecules. This yields the second peak conductance listed for these molecules in Table 1. Consequently, high conductance can be obtained over long distances (13 nm) if proteins are chemically tethered to both electrodes.

This threshold for the onset of voltage-driven fluctuations of about 100 mV has been found for a number of proteins studied to date. Thus, by operating the junction below this threshold for the onset of spontaneous fluctuations (i.e., V<VC in FIG. 4, where VC is about 100 mV) a DC current serves to indicate that a protein is trapped in its quiescent state. This signal is quite large: on average 75 pA at 50 mV bias for the example just given, and substantially more if the protein is chemically tethered so as to bridge the electrode gap.

Figure 2A:
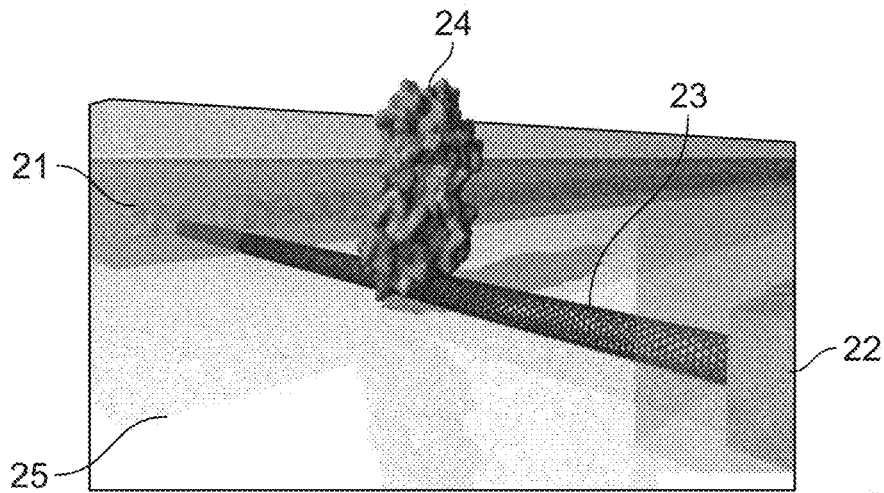
FIG. 2A shows a known detection system for Lysozyme fluctuations according to Choi et al.
Figure 2B:
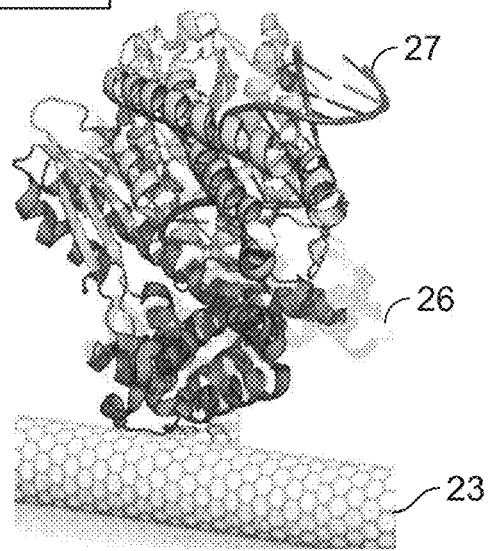
FIG. 2B shows a known detection system for polymerase fluctuations according to Olsen et al.
Figure 2C:
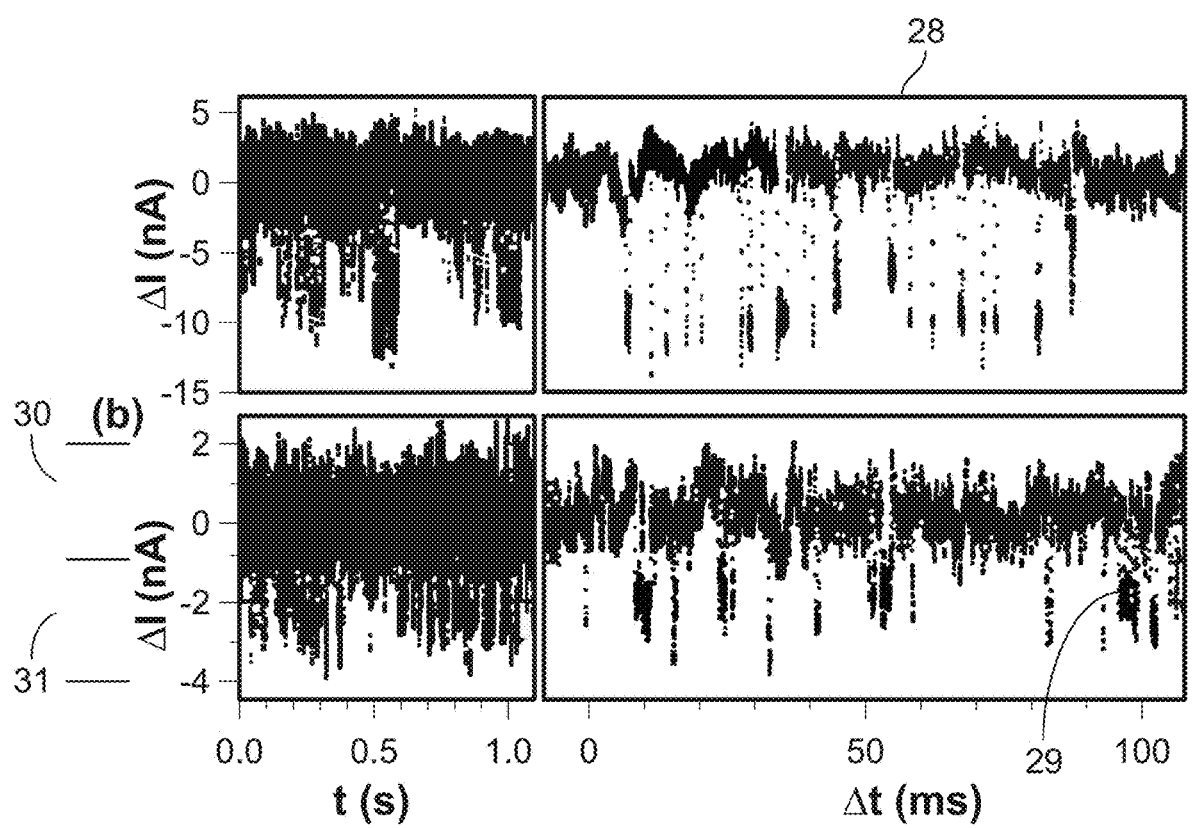
FIG. 2C shows nucleotide sequence dependent data according to Olson et al.
Figure 2D:
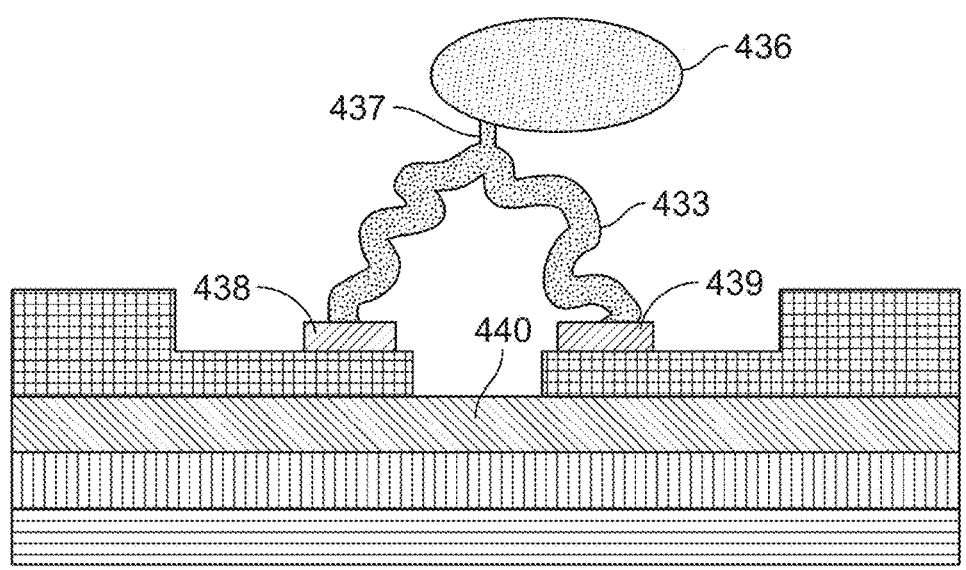
FIG. 2D shows a known detection system for polymerase fluctuations according to Merriman and Mola.
Figure 3:
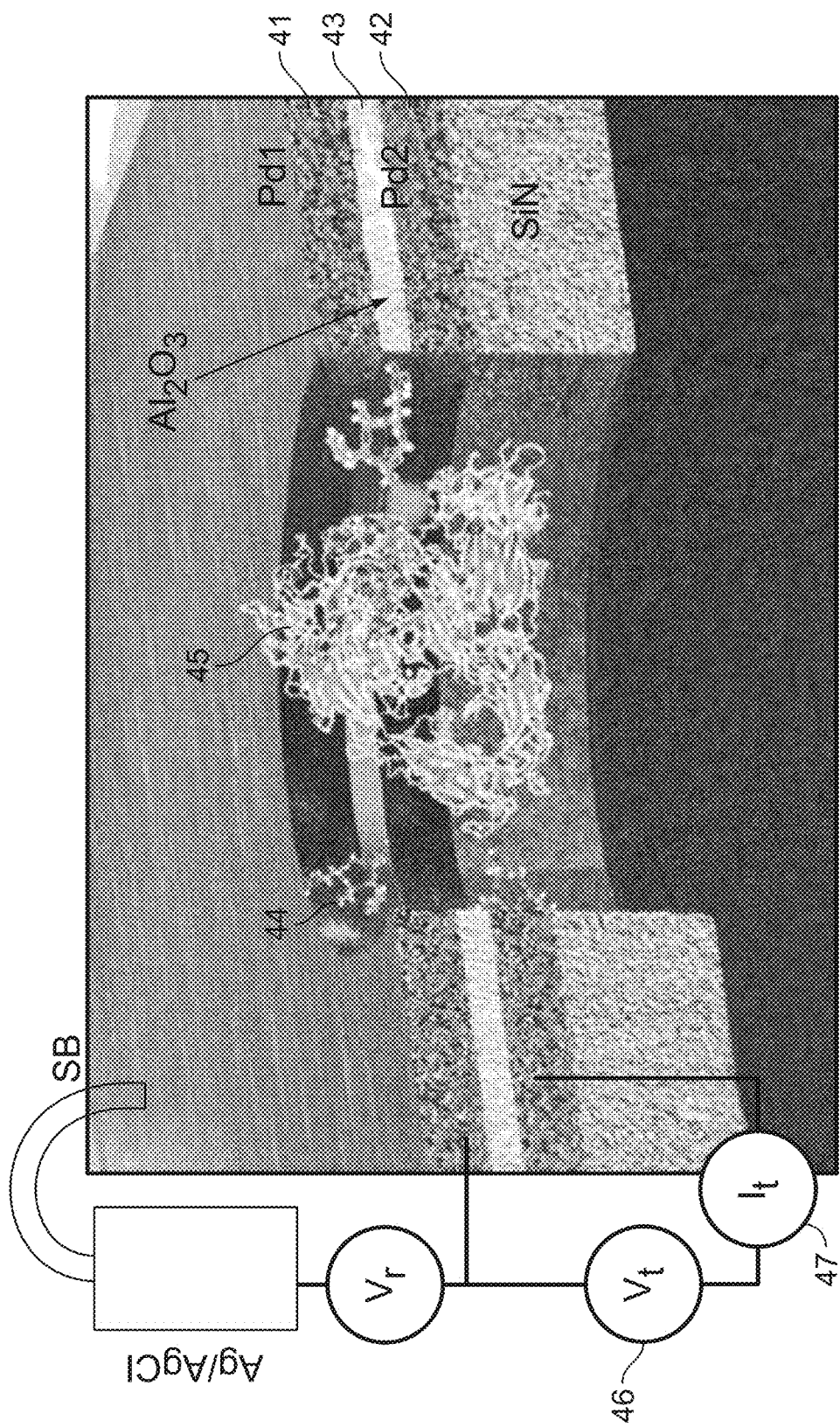
FIG. 3 shows a known device for protein detection.
Figure 6:
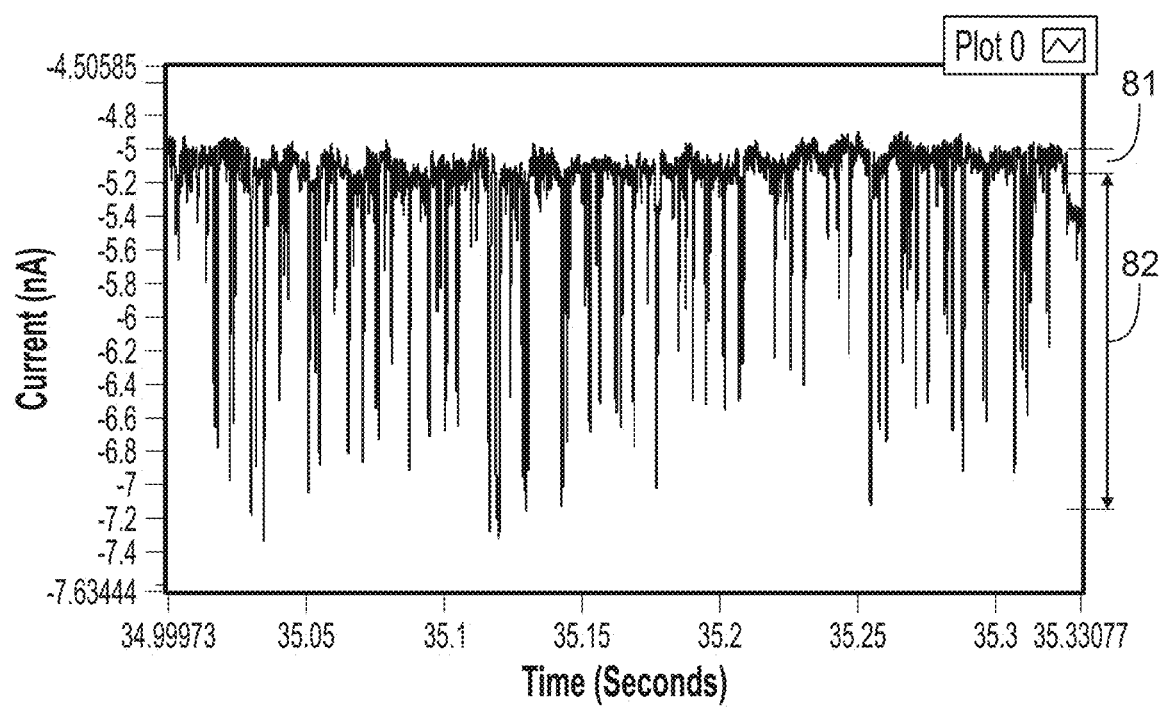
FIG. 6 shows signals representative of protein fluctuations.

Protein fluctuations open up additional channels for electron transport. Thus, when a protein is biased below VC but stimulated by introducing a substrate molecule, large current fluctuations can occur. An example of the current signals induced by protein fluctuations is shown in FIG. 6. Note the greatly improved signal 82 to noise 81 compared to that shown in FIG. 2C. A further example of induced protein fluctuations is given in FIG. 12. This shows data collected by an STM probe held at a constant 3.5 or 4.5 nm height above a monolayer of phi29 polymerase coupled to a palladium electrode via a biotinylated N-terminus binding thiolated streptavidin molecules bound on the electrode surface. Panels A, B and C show the fluctuations in current that occur as a result of fluctuations in the contact point with the polymerase. Over time (insets to right) this can lead to large changes in current but ms-timescale telegraph noise is not observed if the bias is below VC. The expanded current-time traces on the left are taken from the peak current regions (circled in red on the long-time scale plots inset on the right). When primed, single-stranded DNA template and dNTPs are added, ms-timescale telegraph noise is induced, as shown in panels D, E and F.

Figure 14:
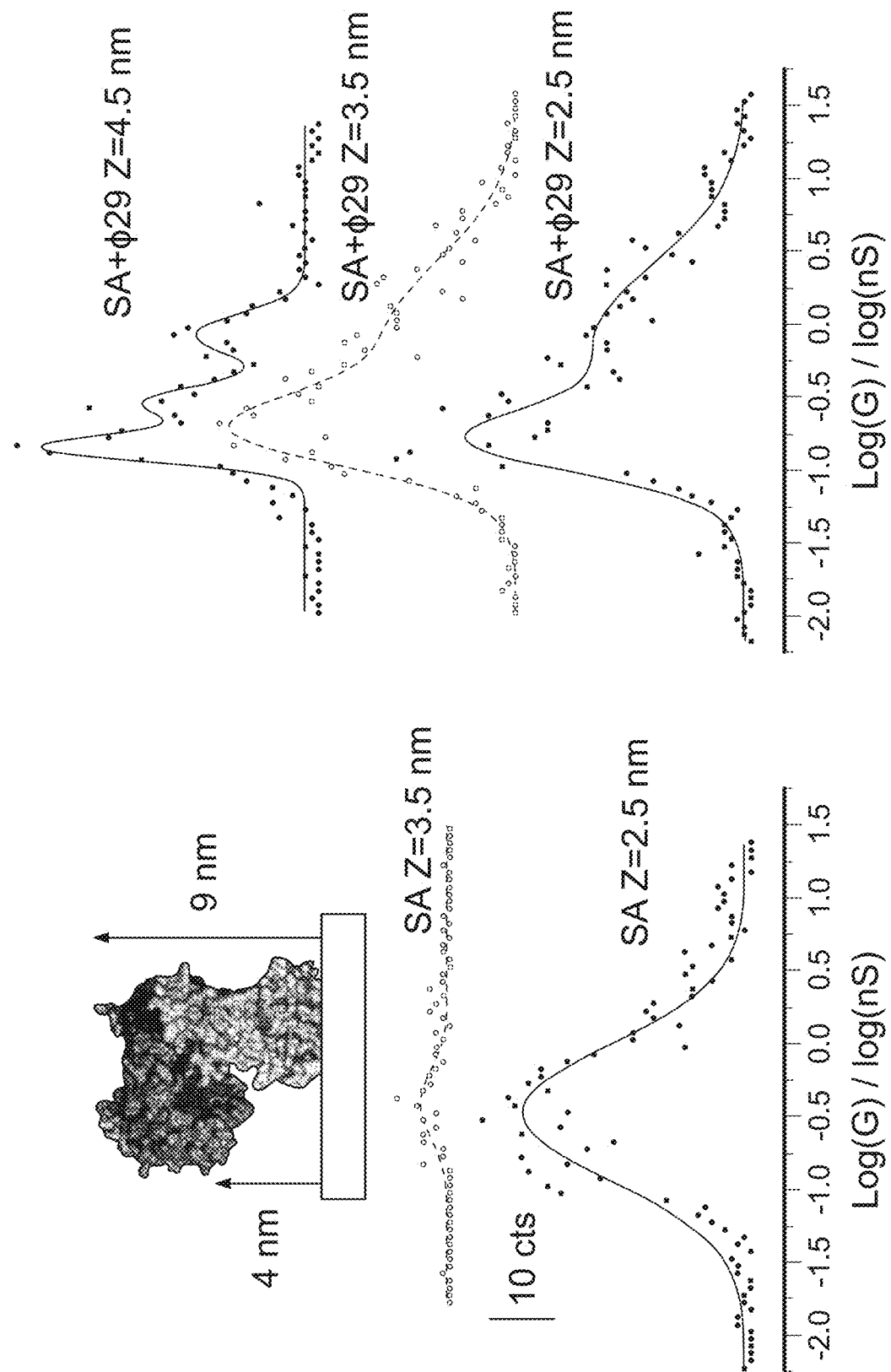
FIG. 14 shows gap distance-dependence of conductance distributions for (left) streptavidin and right, a streptavidin-polymerase complex taken at different gap sizes as marked. The conductance distributions change little with gap size, showing that conduction in these proteins is by a delocalized transport mechanism. Inset shows estimates of the protein heights—the streptavidin is about 4 nm high, and complex of phi29 bound to streptavidin is about 9 nm high. Signals were obtained from gaps as big as 5.5 nm showing that the conduction path must be, in part, through the phi29, although the probe is almost certainly in contact with the polymerase interior in these data sets.

The signals shown in FIG. 12 were taken with a single chemical attachment point for the polymerase. In consequence, the connection to the second electrode is highly variable, as shown by the current fluctuations in FIGS. 12 A, B and C. Another important drawback of a single chemical contact is the poor performance of the physical contact between the protein and the second electrode. This is illustrated in FIG. 14. This shows conductance distributions measured over a streptavidin monolayer (left side) and over the same monolayer after binding biotinylated phi29 polymerase (right side) as the electrode gap is increased in 1 nm increments for gap values as marked (the distribution curves are displace vertically for clarity). For the case of streptavidin, very few curves are recorded at a gap distance of 3.5 nm. For the case where phi29 is bound to the streptavidin, curves are recorded out to 4.5 nm (with a few recordings at 5.5 nm—not shown). However, this is substantially smaller than the overall height of the polymerase-streptavidin complex of about 9 nm (shown in the inset). This stands in sharp contrast to the antibody data shown in FIG. 13 where high conductances were obtained over the 13 nm path that separates the two binding domains. This demonstrates the desirability of forming two chemically well-defined contacts, one to each electrode in the pair.

Methods of Making a Device of the Disclosure

A device of the disclosure can be readily fabricated by depositing a layer of a noble metal such as Au, Pt or Pd onto a silicon, glass or sapphire wafer (or other dielectric substrate), then depositing a thin (typically 1 nm) layer of a reactive metal for adhesion (such a s chrome or titanium), and then a layer of 1 to 10, or 1 to 20 or 1 to 50 nm of the noble metal. This bottom electrode is than covered with an insulating dielectric layer, preferably alumina, though other oxides such as $SiO_2$ or hafnium oxide can be used. The layer should be between 2 and 10 nm in thickness. A 2 nm layer can be deposited by coating the bottom noble metal electrode with 1 to 1.5 nm of aluminum, and allowing it to oxidize in air, thereby producing a 2 to 3 nm thick layer of $Al_2O_3$. If a greater thickness of dielectric is required, further $Al_2O_3$ can be added by atomic layer deposition with water/trimethylaluminum cycles as is well known in the art.

A second noble metal electrode is then deposited, again using a thin adhesion layer (chrome or titanium) but of a maximum of 1 nm so as not to alter significantly the gap presented at the edge of the device where this adhesion layer will oxidize.

Finally, a passivation layer is placed on top of the top electrode. This can be alumina, $SiO_2$, hafnium oxide or a resist material such as PMMA or SU8.

In order to make a cavity small enough to ensure that the exposed electrode area is such that only one polymerase is attached, a small opening is then made using Reactive Ion Etching (RIE) as is well known in the art. This opening may be between 10 and 500 nm in diameter with about 50 nm preferred. The depth of the opening should be large enough so that it cuts through the passivation layer, the top electrode, the dielectric layer separating the electrodes, and into the bottom electrode.

A second way to limit the amount of exposed electrode area is to make one of the electrodes (top or bottom, with top preferred) a thin wire of 50 to 100 nm in width. The RIE opening can then be much larger (e.g., micron sized permitting conventional lithography) because the exposed electrode will be limited by the small width of the electrode.

A third way is to control the functionalization chemistry by controlling the amount of time that the junction is exposed to polymerase molecules and/or the concentration of polymerase. The loading of each junction can be tested by monitoring the telegraph noise that is induced by contact fluctuations when the applied bias is above 100 mV. The presence of 2 signal levels indicates that just a single molecule is trapped. The presence of three levels indicates that two molecules are trapped and so on. In this way the concentration and exposure time can be adjusted an ideal Poisson loading wherein about 30% of the sites are singly occupied.

After cleaning with an oxygen plasma, the exposed area of the electrodes in the opening can be functionalized with protein. This may be either directly, using the native thiols on the surface of the protein, or via chemical modifications that attach sulfhydryl groups to the protein, or indirectly, by attaching a thiolated streptavidin and then capturing a biotinylated protein.

A second approach to making the device is to form the two electrodes in the same plane with a small gap between them. This can be done by opening a trench across a single wire using e-beam lithography and lift-off or reactive ion etching (RIE) as is well known in the art. Other approaches are to use helium ion milling, or angled deposition of metal over a step edge so that a gap is naturally formed. The electrode pair are then covered with a passivation layer and an opening formed by RIE such that the electrode gap is exposed. The electrodes can then be functionalized as described above.

The width of the exposed electrodes is important, because the devices described here generally rely on connecting to just one molecule. In the case of extracting sequence information, this requirement of a single molecule signal is particularly important. If the electrodes are not much wider than a single molecule (5 to 15 nm) then attachment of multiple molecules across the gap is not possible. However, reliable functionalization and fabrication of such small electrodes is very difficult. In practice, we have found that electrodes of up to 100 nm width are unlikely to capture more than one protein molecule. In particular, when the probability of binding in the desired (bridging) configuration is small, it may even be desirable to have even wider electrodes, of 200, 300, 400, 500 or even 1000 nm width. Protein molecules that are bound to just one electrode, rather than bridging the pair of electrodes, will contribute relatively small amounts of current.

Methods of Attaching a Polymerase to the Electrodes

When the protein is a polymerase, it should be a polymerase with high processivity, such as the phi29 polymerase, and its exonuclease function should be disabled as described below.

The wild-type (WT) polymerase requires modification to (a) remove its exonuclease activity and (b) add a chemical attachment point if so desired. This modification is achieved by recombinant DNA using an *E. Coli* expression system to produce the modified polymerase.

Exonuclease activity of phi29 requires the following acidic amino acids: D12, E14, D66 and D169. Mutating any one of these will eliminate the exonuclease activity, and we have mutated D12 and E14 to alanine.

The clone we used has both the his-tag and the avitag (for biotinylation) at the N-terminus, ie His-Avitag-Phi29. As a result, the following sequence was added to the N-terminus of the enzyme:

MGSSHHHHHHSSGLVPRGSGLNDIFEAQK-IEWHEGASS.

Figure 8A:
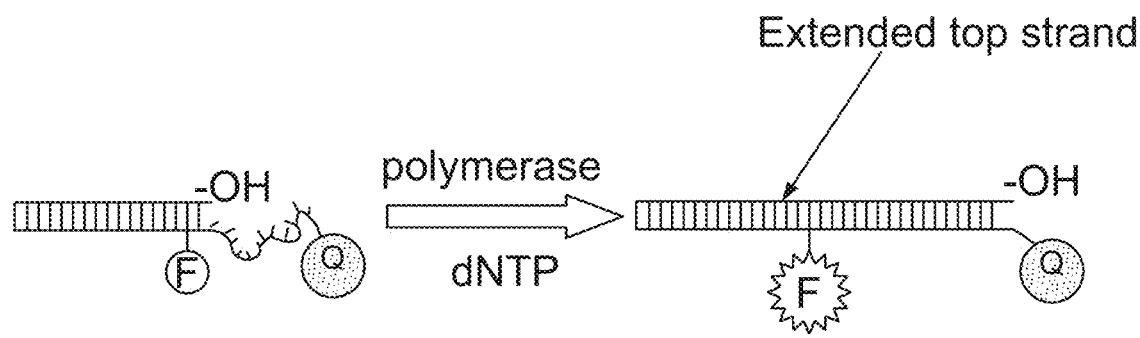
FIG. 8A shows the principle of the fluorescence activity assay used to measure polymerase activity. FAM (F) fluorescence is quenched unless polymerase activity is present.
Figure 8B:
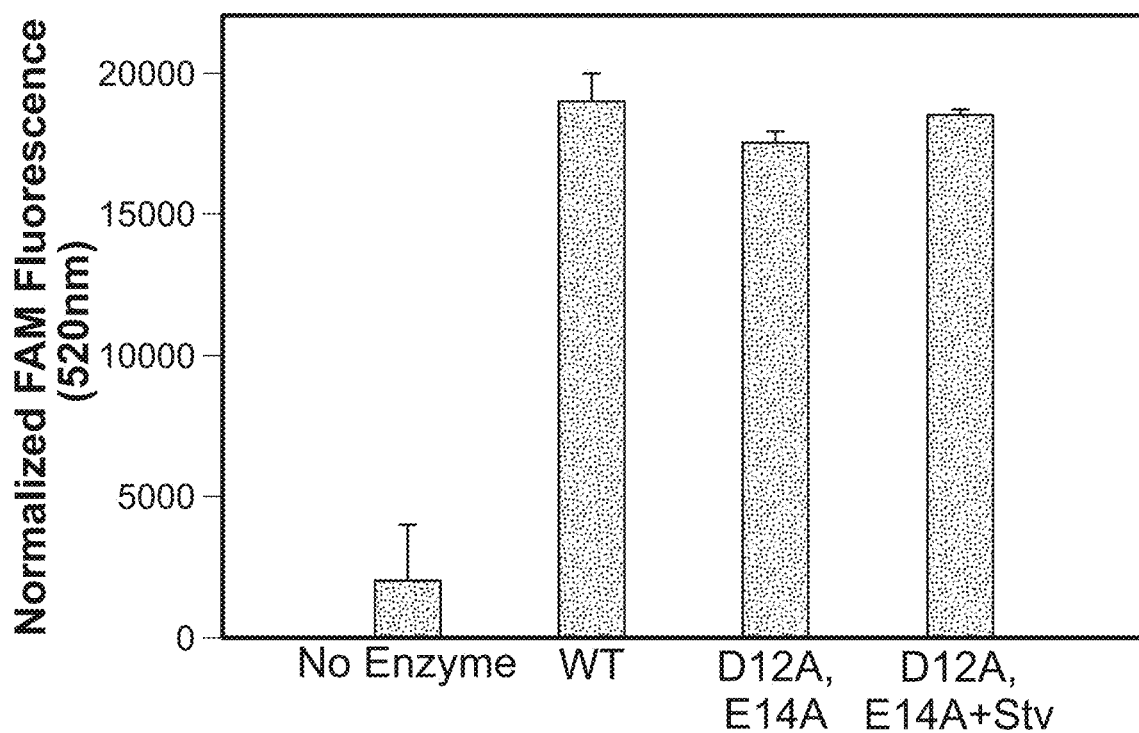
FIG. 8B shows the fluorescent intensity of FAM on the substrate after 60-minute incubation with wild type, exonuclease-free (D12A, E14A) or exonuclease-free enzyme attached to streptavidin.

The six histidine residues are the his tag (used for purification of the desired enzyme product) and the GLN-DIFEAQKIEWHE is the Avitag. The biotin is attached to the K in the avitag by the biotin ligase BirA (Avidity, Lansing, Mich.). Activity assays show that the biotinylated enzyme attached to streptavidin is still active (FIG. 8B).

Another useful and unexpected feature of the present disclosure is that both streptavidin and polymerase are conductive proteins, so, as we show below, the polymerase can be attached to the electrode indirectly. First a streptavidin, modified with thiols, is attached to the electrode, and then biotinylated polymerase introduced. This binds to the streptavidin, providing a conductive path to the electrode.

The polymerase can also be modified at the C-terminus by the same recombinant methods. In addition to the avitag, other peptide-based binding tags can be used such as GST tags, Myc tags and His tags. These tags can all be incorporated at either the N- or C-terminus of the polymerase. Incorporation at the C terminus places the tag site close to the site at which a primed template is captured, so oligo-alanine or glycine-glycine-serine spacer sequences can be incorporated between the C terminus and the tag to reduce interference with the template capture activity of the polymerase.

The same technology can also be used to attach other proteins whose activity is to be monitored using the methods of the present disclosure (such as kinases, proteases or molecules that process glycans).

In addition to modification at the N- or C-termini, there are seven cysteines in phi29. None are disulfide bonded, so all have the potential for forming disulfide bonds, offering additional sites for attachment to electrodes. Based on the structure of phi29 with template and primer C448, C106 and C22 are most surface exposed and look like good candidates for either biotinylation through maleimide or direct attachment to heavy metals that bind sulfhydryl groups. The problem is how to control specificity. We tried to mutate out all but one cysteine once, but the result is insoluble protein. However, up to four may be removed without affecting solubility, leaving C448, C106 and C22 as targets for attachment points.

Although the present disclosure works with just one chemical attachment site to one electrode, the second contact being made by physical contact between the protein and the metal, it is desirable to make two chemically well-defined contacts in a manner that spans the gap between the two electrodes. The C terminus is separated from the N terminus by a distance of ~5 nm, and if biotinylation via an avitag is used, attachment to the same streptavidin molecule by both the N- and C-termini of the same polymerase is improbable. Thus, with both electrodes functionalized with thio-streptavidin, there is an opportunity for bridging structures to form in which the N terminus is connected to one electrode and the C terminus to the second electrode.

Figure 15:
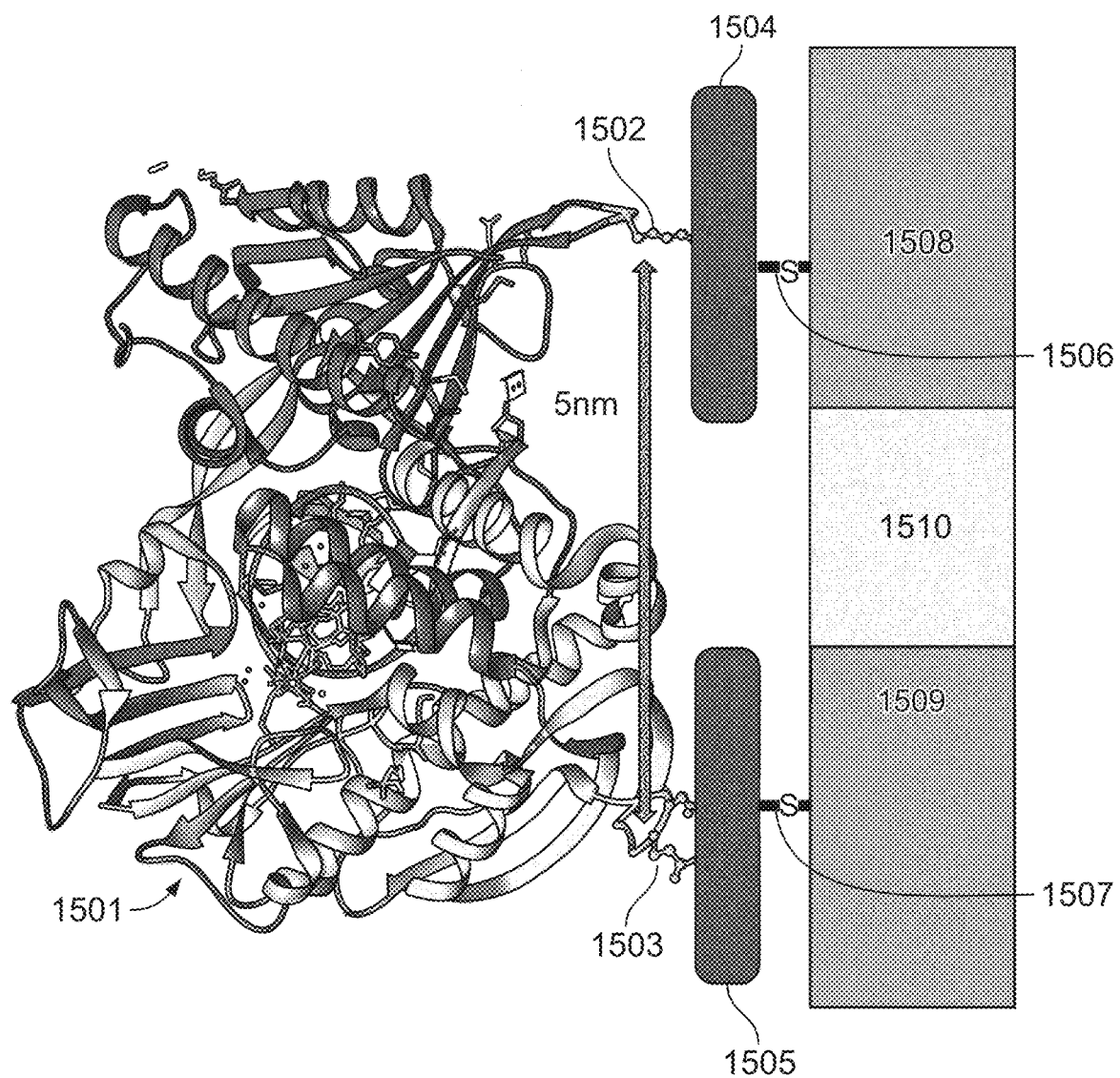
FIG. 15 shows attachment of a polymerase via two biotinylated sites on the polymerase, separated by 5 nm, to two streptavidin molecules on the electrodes. The streptavidin molecules are coupled to the electrodes via thiol moieties.

Another approach is to use two attachment points that are widely spaced, but in an inactive region of the protein. In the case of phi29 polymerase, where the exonuclease domain has been disabled by mutations of D12 and E14, two points in the exonuclease domain spaced by >5 nm are found between G111 and K112, and between E279 and D280. Accordingly, with the Avitag sequence GLNDIFEAQK-IEWHE inserted at these two points, and the Avitag lysine biotinylated by BirA, the polymerase can be bound across a pair of electrodes as shown in FIG. 15. This shows a phi29 polymerase 1501 that is biotinylated using Avitags place between G111 and K112, and between E279 and D280 (1502 and 1503). These biotins bind thiolated streptavidin molecules 1504 and 1505 that are attached via sulfur linkages 1506 and 1507 to the electrodes 1508 and 1509. Since gap between these attachment points (double headed arrow on FIG. 15) is a little over 5 nm, this attachment geometry requires a gap 1510 of a little under 5 nm.

Making Deterministic Contacts Between Polymerases and Electrodes by Adding 'Conducting Whiskers' to the Polymerase.

At the N terminus add recombinantly:
CGSSHHHHHHSSFTLIELLIVVAIIGILAA-IAIPQFSAYRVKAYNSAASSDRLNLKTA LESAFA-DDQTYPPESGLVPRGSGASS-f29

The terminal C is the cysteine for attachment to the first electrode.

The his tag is for protein extraction and purification.

The 61-amino acid sequence following SS is the sequence of the pilus protein from geobacter sulferreductans, which acts as a metallic wire.

At the C terminus add recombinantly:
f29-AAFTLIELLIVVAIIGILAAIAIPQFSAYRVKAYN-SAASSDRLNLKTALESAFADDQT YPPESC The 61-amino acid sequence following AA is the sequence of the pilus protein from geobacter sulferreductans.

The terminal C is the cysteine for attachment to the first electrode.

Conductivity of the Complex

Figure 9:
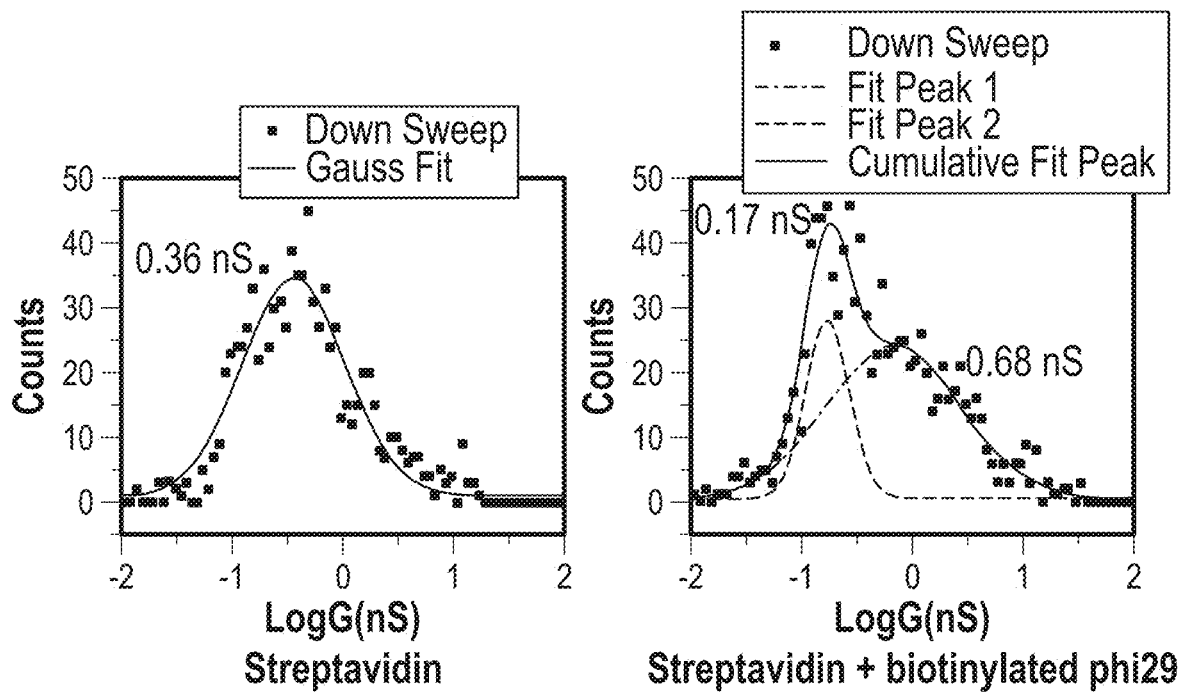
FIG. 9 shows distribution of conductances measured for (left) thiolated streptavidin and (right) after attachment of biotinylated phi29 polymerase. The streptavidin measurements were made at a gap of 2.5 nm and the streptavidin plus phi29 measurements were made at a gap of 3.5 nm.

Key to the present disclosure is that good electronic conductance can be obtained through the polymerase. FIG. 9 shows (left panel) a distribution of conductances through streptavidin connected to the substrate via thiol bonds. These data were taken with an electrode gap of 2.5 nm. If the gap is increased to 3.5 nm, very few reads occur. If the gap is further increased to 4.5 nm, no reads at all are obtained. This is consistent with the fact that a streptavidin molecule, lying flat on the surface, is about 4 nm high. The right-hand side of FIG. 9 shows data for a complex of biotinylated phi29 polymerase with streptavidin on a Pd electrode. These data were obtained at a gap size of 3.5 nm. Similar data were recorded at a gap size of 4.5 nm for the complex (a gap where no conductance was recorded for the streptavidin). Since these distances are larger than the gaps at which the streptavidin alone gave robust signals, they show that conduction is occurring through the polymerase wired in series with the streptavidin. Note how the distribution of conductances is altered in the complex compared to streptavidin alone.

Conductivity Changes with Conformation

Figure 10:
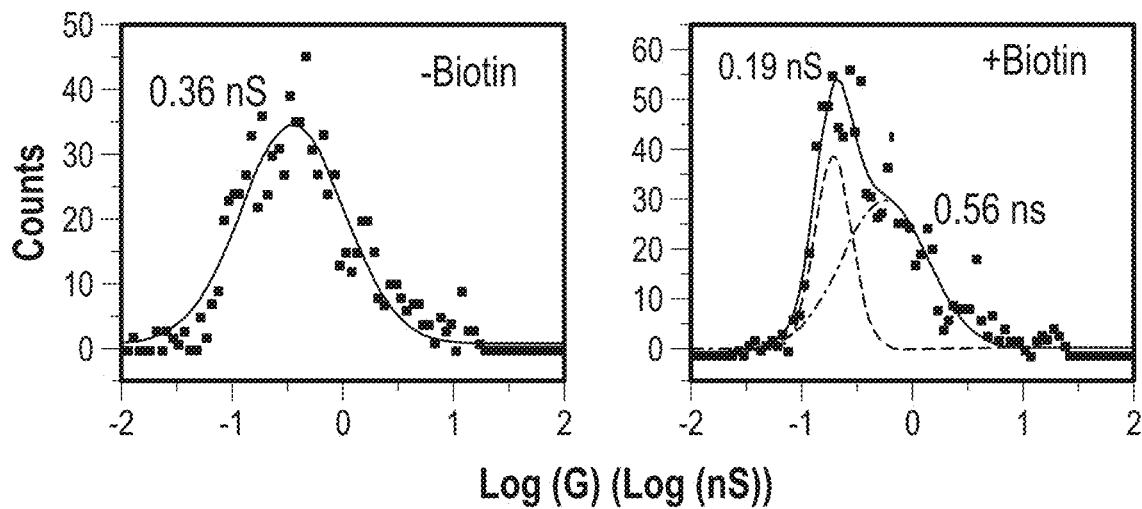
FIG. 10 shows conductance changes with conformation. Left panel is for thio-streptavidin and the right panel is data taken from the same film of molecules after biotin was added. The conductance changes showing that it is sensitive to the conformational changes induced by biotin binding.

FIG. 10 shows a measured distribution of conductances for streptavidin alone (left panel) and streptavidin after exposure to biotin. The distribution of measured conductances changes after the streptavidin binds biotin, showing that the conductance of the protein is sensitive to changes in protein conformation.

Dynamic Monitoring of Protein Conformation

Figure 11:
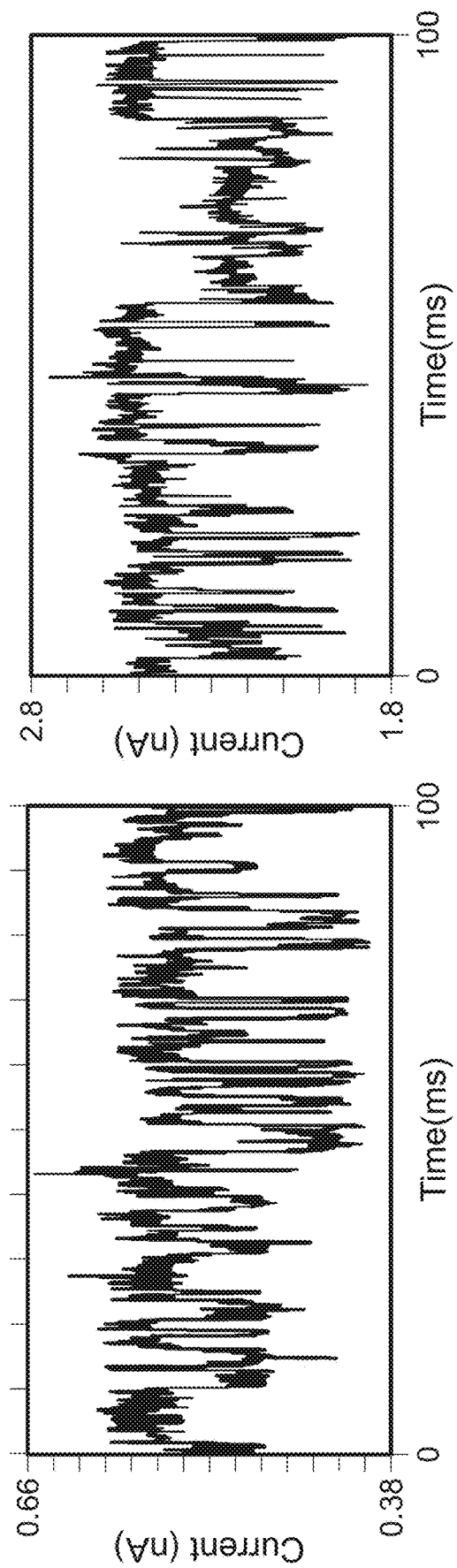
FIG. 11 shows high contrast, high time-resolution recordings of protein fluctuations in (left) and STM gap and (right) a solid-state chip. The sample is anti-DNP IgE with DNP on the electrodes. The devices are operated at 200 mV with a gap of 4.6 nm.
Figure 12A:
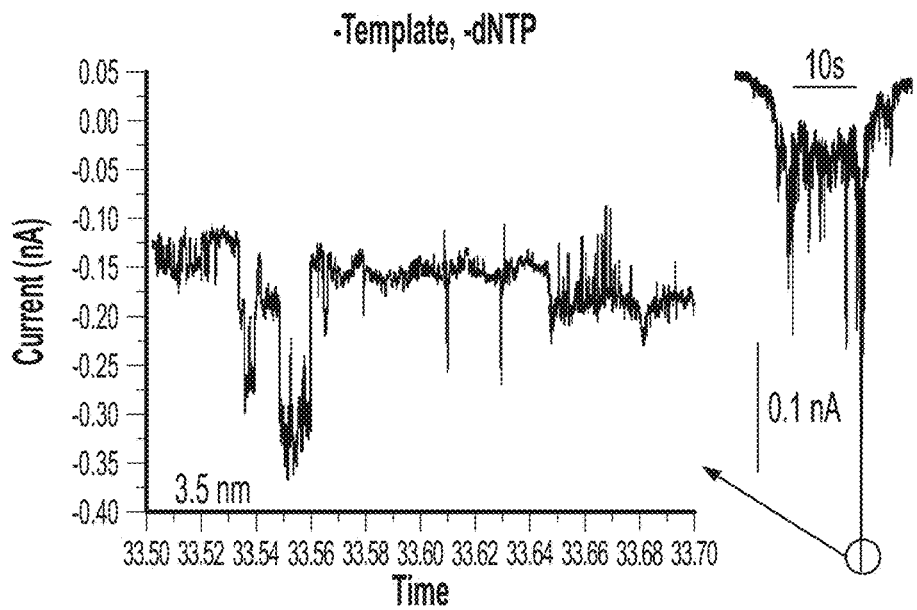
FIG. 12 shows current collected at constant gap (as marked lower left on each panel) and 50 mV bias on phi29-streptavidin complex showing just contact fluctuations in the absence of template DNA and dNTPs (A,B,C) and the additional telegraph noise that appears when template DNA and dNTPs are added (D,E,F). Insets to right show full runs over 20 to 40 s duration. The red circle denotes the high current point expanded in the traces on the left.
Figure 12B:
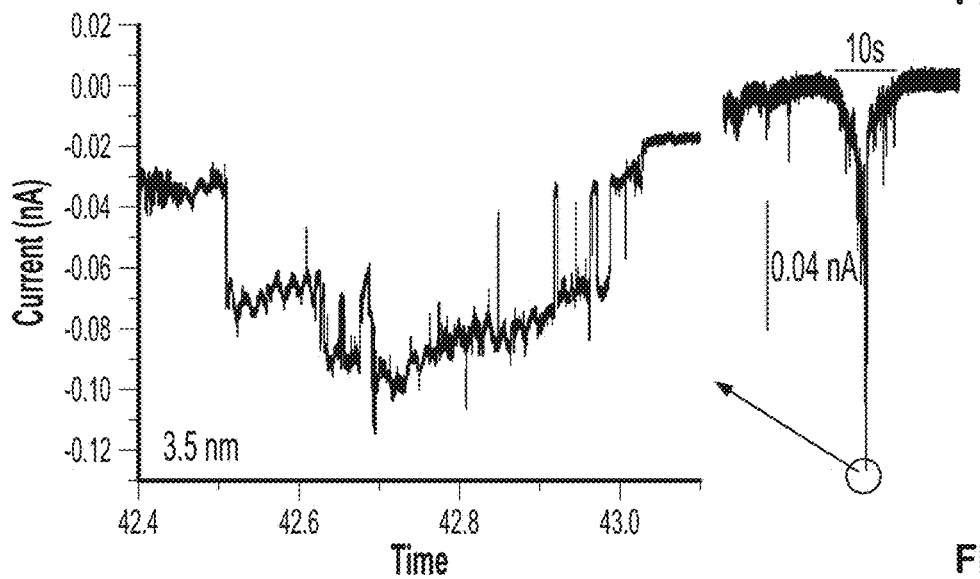
Figure 12C:
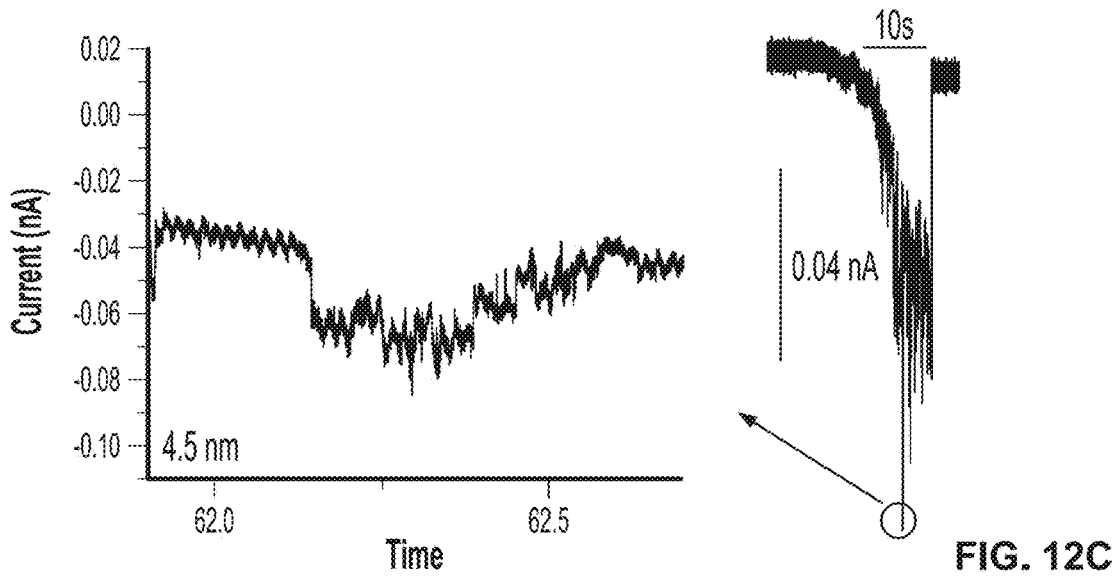
Figure 12D:
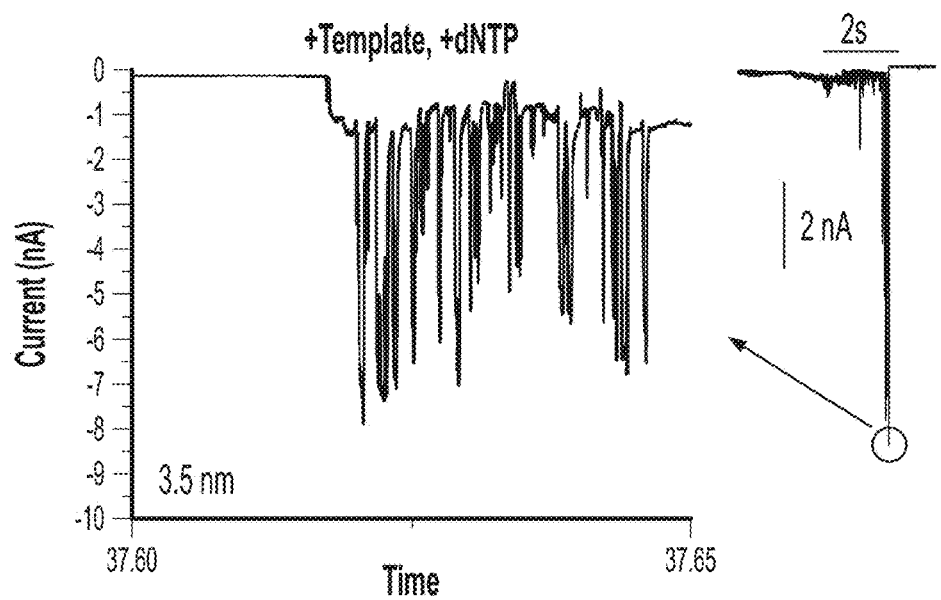
Figure 12E:
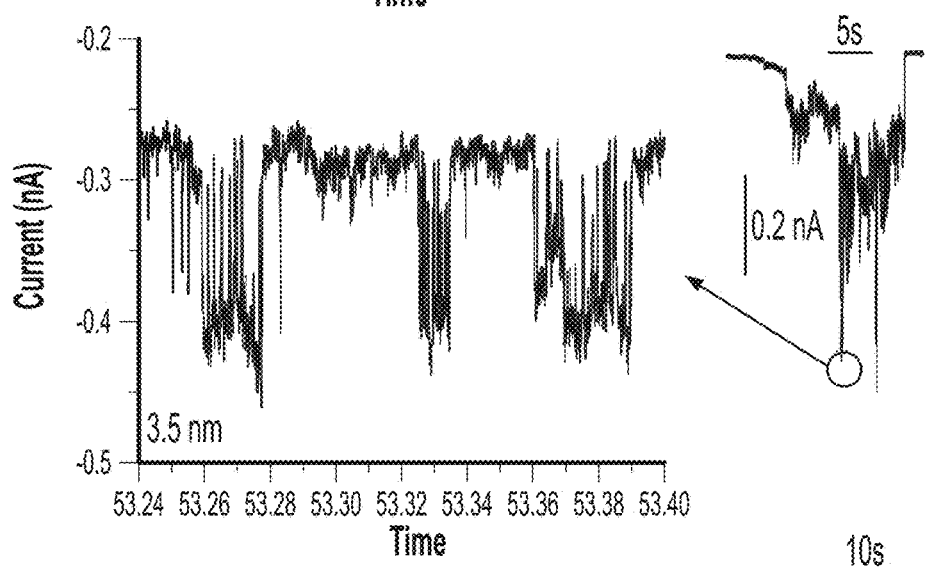
Figure 12F:
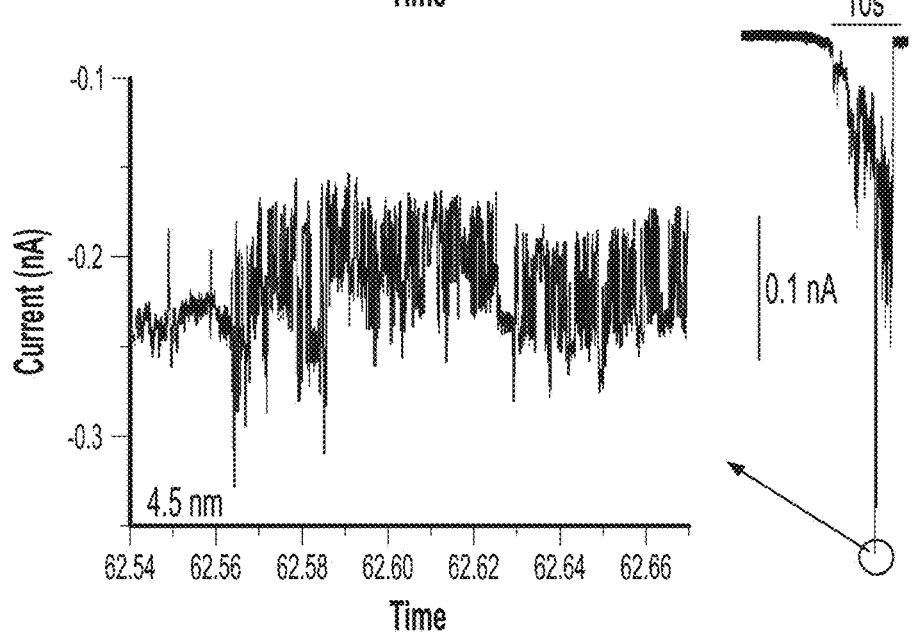

FIG. 11 shows a recording of voltage-induced conformational fluctuations recorded (left panel) with a scanning tunneling microscope and (right panel) with a solid-state chip using a gap of 4.5 nm. The bias was 200 mV, 100 mV above VC. The protein is an anti-dinitrophenol molecule binding dinitrophenol (DNP) attached to the electrodes. Very large changes in conductance on the millisecond timescale are readily recorded with excellent signal to noise ratio. FIGS. 12D, E and F show the fluctuations in current that occur when the bias is reduced below VC (to 50 mV in this case) and the protein activated by addition of substrate. Telegraph noise is generated on ms timescales with very high signal-to-noise ratio.

Methods of Use of the Devices and Systems

Figure 7:
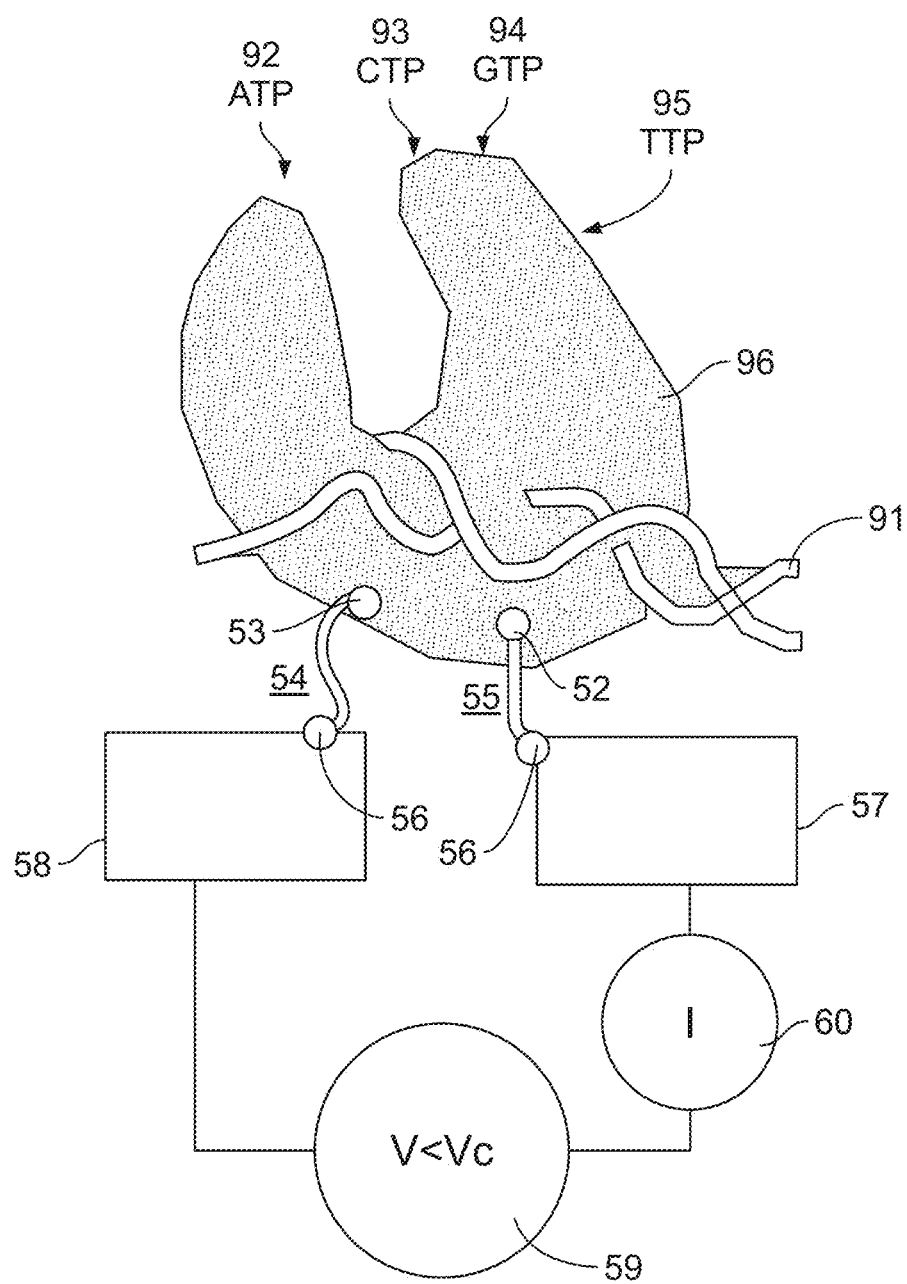
FIG. 7 shows a schematic diagram of an embodiment of the disclosure in which the protein is a polymerase.

The present disclosure provides methods for sequencing a biopolymer. We illustrate this for the specific case of a nucleic acid chain being extended by a polymerase in FIG. 7. Here, a polymerase 96, is modified at two points 53, 52. A specific example would be the two surface-exposed cysteines available in phi29 polymerase. Another example is the biotin functionalization shown in FIG. 15. Maleimide modified alkanes or PEG linkers 54, 55, are used to attach the polymerase to the electrodes 57, 58 via strong thiol bonds (for example) 56. The binding of the polymerase in the electrode gap is verified by means of a steady DC current 60 when V<VC 59. When the polymerase 96 is complexed with a primed template 91 and exposed to a solution comprising each of the four nucleotide triphosphates 92 93 94 95, characteristic current fluctuations will signal the incorporation of a given nucleotide. In an alternative embodiment, surface cysteines could be used to make one of the attachments directly.

In use, once the device is prepared, it should be rinsed and then exposed to the primed template DNA to be sequenced. This DNA is prepared from the sample to be sequenced by ligating hairpin primers as well known in the art. A buffer solution comprising the four dNTPs and $Mg^{2+}$ should be introduced to the device. The dNTPs are present in the buffer solution in about equal concentration. In one embodiment, the concentrations of dNTPs are about equal to the saturation concentration of template-bound polymerase, at the saturation of concentration of template-bound polymerase in a second embodiment, and above the saturation concentration in third embodiment. When the concentrations of dNTPs are at or above the saturation concentration, the polymerase runs fast (i.e., 100 nucleotide incorporations per second).

When the buffer solution comprising the dNTPs is introduced to the device, a polymerization reaction will be initiated and the captured template will be copied to the primer, producing a series of current spikes. Each spike (or cluster of spikes) occurs as each new nucleotide is incorporated to the primer, and the characteristics of each spike (duration, amplitude, shape) used to decode the identity of the nucleotide being incorporated. A typical sequencing speed at saturation concentration (>30 μM) of nucleotides is about 100 nucleotides per second. The saturation concentration of template is about 10 nM with a new template incorporated almost immediately after completion of the previous template. Each molecule will continue to turn over template so long as there are templates available in solution. Therefore, one molecule can sequence continuously for as long as the device is operated.

The device geometry is extremely simple with no need to separate fluidic compartments for each junction, so one junction would only occupy about a $micron^2$. Allowing for interconnects, isolation and on-chip processing electronics, a single reading device could readily be fitted into an area of 100 microns by 100 microns, so an active chip area of 1 $cm^2$ would accommodate 10,000 devices. A chip with 10,000 junctions on a chip operated for 1 hour would sequence an entire human genome ($10000 \times 3600 \times 100 = 3.6 \times 10^9$). A denser device geometry or a larger chip would accommodate even a significant fraction of inactive devices and still permit genome-scale sequencing on one small device in times of an hour or less.

The preceding example illustrates the sequencing of nucleic acid polymers, but it also can be applied such that other enzymes that process polymers could be used. For example, current fluctuations in an exonuclease will reflect the composition of the nucleic acid they are degrading. The same would be true of proteasomes that digest peptides. An example is the proteasome 20S CP, and proteasomes like this could likely be used for single molecule peptide sequencing by incorporating them into the system of FIG. 4 and monitoring the electrical signals generated when they are fed peptide molecules and biased be low VC.

Similar enzymes, called glycosidases, exist for digesting glycans. The incorporation of a glycosidase into the device of FIG. 4 would allow electronic sequencing of glycans. The variation in bonding of glycans might preclude a direct linear read out of sequence, but the organization of cutting events in time may allow for identification of the glycans.

In yet another embodiment, the present disclosure provides a method for detecting kinase activity. In this embodiment, a kinase is incorporated into the device of FIG. 4, exposed to its substrate, and kinase activity signaled by the generation of large current fluctuations when biased below VC. The system could then be exposed to candidate kinase inhibitor drugs as the fluctuations are monitored, to discover which drugs "kill" the activity of the kinase. In the present art, the use of fluorescence labeling methods may interfere with a protein enzyme interacting with its substrate, and the present disclosure removes the requirement for labeling of proteins.

In all of these methods, the use of a simple junction (as opposed to a FET structure) greatly simplifies both manufacture and enables scale up to large parallel arrays of devices. The device of the disclosure may be prepared in massively parallel fabrication using methods for scalable fabrication of junction devices, as described below.

Arrays and Systems for Sequencing DNA or Other Polymers

The present disclosure provides an array for sequencing biopolymers using any of the enzymes that interact processively with molecular templates such as a nuclease, a proteasome, a glycopeptidase, a glycosidase, a kinase and an endonuclease. The embodiments below illustrate an array for sequencing DNA using a polymerase. It should be understood that any processive enzyme can be substituted for the polymerase in the arrays.

The array comprises an arrangement of a plurality of devices. The device used in the arrays of the present disclosure include the following.

In one embodiment, the device comprises a first and a second electrode, the first and second electrode being separated by a gap; and a polymerase attached to one or both electrodes; wherein the first electrode and the second electrode have an opening formed therethrough.

In another embodiment the device comprises a first and a second electrode, the first and second electrode being separated by a gap; and a polymerase attached to both the first and second electrode.

In some embodiments, the device comprises:
  (a) a dielectric substrate;
  (b) a first electrode disposed on the dielectric substrate;
  (c) an insulating dielectric layer disposed on the first electrode;
  (d) a second electrode disposed on the insulating dielectric layer;
  (e) a passivation layer disposed on the second electrode;
  (f) a polymerase molecule attached to the first and second electrodes;
  wherein the first electrode, the insulating dielectric layer, the second electrode and passivation layer have an opening formed therethrough.

In some embodiments, the device comprises:
  (a) a dielectric substrate;
  (b) a first electrode disposed on the dielectric substrate;
  (c) a second electrode disposed on the dielectric substrate;
  (d) a passivation layer disposed on top of the electrodes; and
  (e) a polymerase molecule attached to one or both the electrodes;
  wherein the passivation layer has an opening formed therethrough.

In some embodiments, the device comprises:
  (a) a first and a second electrode, the first and second electrode being co-planar and separated by a gap;
  (b) a protein attached to at least one electrode;
  wherein the first electrode and the second electrodes are configured for contact with a sample to be analyzed.

In each of the device embodiments described herein, the first and/or second electrode comprise a metal selected from the group consisting of gold, platinum, palladium, and ruthenium. In some embodiments, the metal is palladium.

In some embodiments, the gap has a width of about 1.0 nm to about 20.0 nm. In some embodiments, the gap has a width of about 1.0 nm to about 10.0 nm. In some embodiments, the gap has a width of about 1.0 nm to about 7.5 nm. In some embodiments, the gap has a width of about 1.0 nm to about 5.0 nm. In some embodiments, the gap has a width of about 4.0 nm to about 5.0 nm.

The array of devices can be arranged in any suitable manner, e.g., in a grid.

In some embodiments, the array comprises polymerase molecules bound with template DNA. Such templates can be made by ligating genomic DNA fragments (generated by sonication, for example) with primer sequences containing a nick for binding by polymerase, as is well known in the art. The result is a library of templates spanning an entire genome, if needed. Each template will then randomly bind one polymerase in the array.

Figure 16:
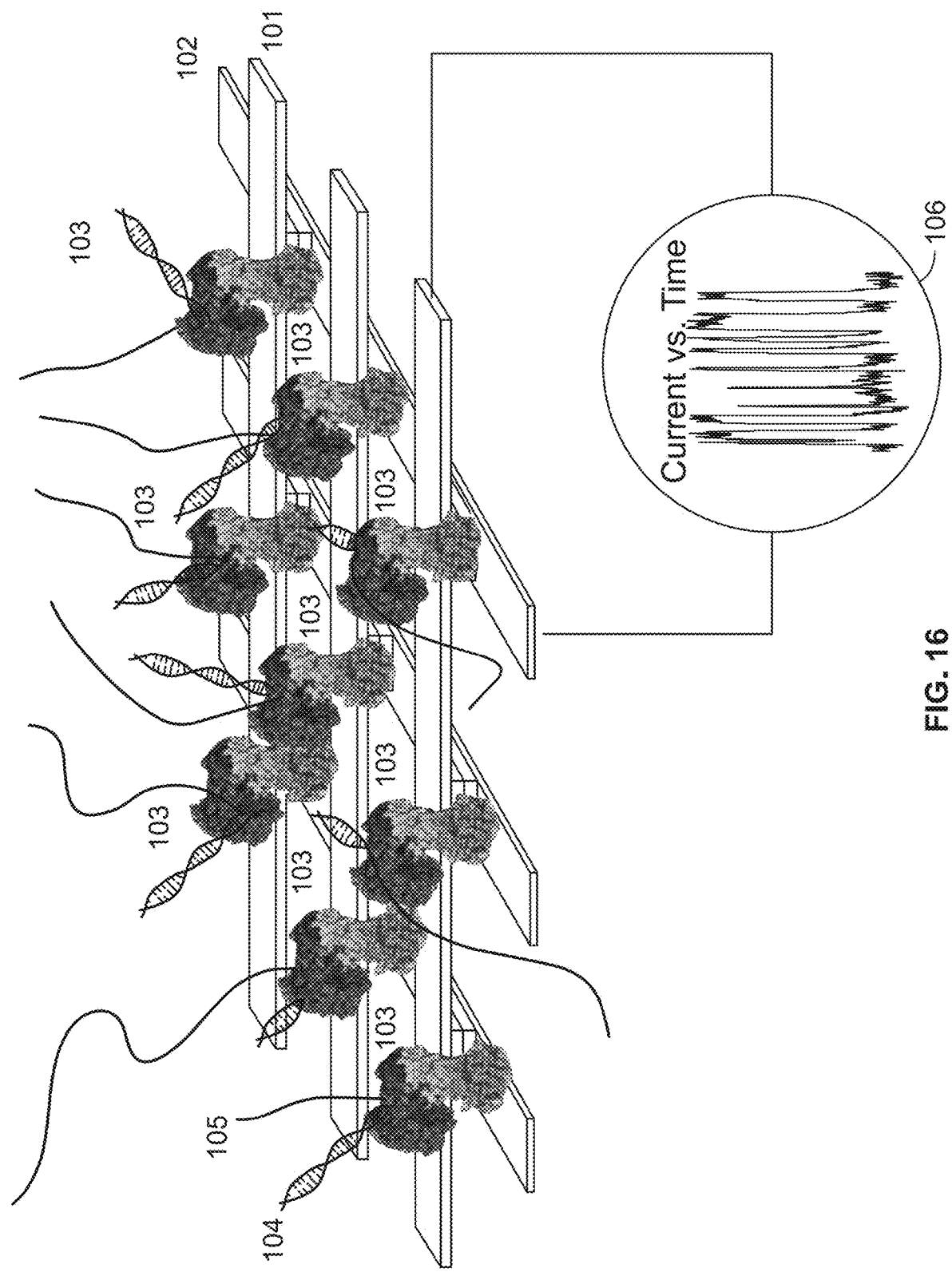
FIG. 16 shows an array of polymerase molecules bound with DNA templates, each polymerase being wired into an individually addressed pair of electrodes.

Referring now to FIG. 16, a grid of contacts 101, 102 is formed from two layers of contact metals separated by a dielectric as is well known in the art, and then covered by a passivation layer. Each intersection is then exposed by selectively removing the passivation, and polymerase molecules 103 bound at each junction. These biomolecular junctions can be prepared by methods discussed in the previous section. By making the electrodes narrow enough (about one micron in width) usually only one polymerase (or none) will bind. In the case where two or a few more bind, the signals can still be deconvolved because they consist of two current levels for one molecule, three for two, and so on.

The present disclosure also provides a system of arrays for direct measurement of polymerase activity. The system comprises an array as described herein; optionally a means for introducing and removing a solution to the array; a means for applying a bias between the first and second electrode; and a means for monitoring the current generated between the first and second electrodes.

Referring back to FIG. 16, means 106 are provided for applying a small bias (typically 50 mV) and reading the current from each junction so that it may be recorded by a computer storage system.

Methods for DNA Sequencing Using a System of Arrays

The present disclosure also provides a method for DNA sequencing using a system of arrays as described herein.

The sequencing proceeds by introducing a solution comprising one nucleotide monophosphate (e.g., one from among dATP, dGTP, dCTP, dTTP) together with magnesium to the array. Each polymerase bound with a complementary nucleotide will generate a signal, which is read by the unique pair of electrodes to which each polymerase is bound. For example, if the added nucleotide is dCTP, then every template bound at a G base will incorporate a C into the extending chain, generating a signal, whereas the other sequences will generate distinctly different signals. For example, a polymerase presented with a non-matching base will generate a brief burst of signal as the mis-matched base is captured, but the signal train will terminate prematurely as the mismatch is rejected and the process of polymerization and translocation is aborted. In contrast, incorporation of a matching base results in a much longer train of pulses as the process of incorporation and translocation is completed. As the second step, the array is rinsed to remove excess nucleotide and a solution comprising the next nucleotide is introduced (for example dATP, so that all site with a T now generate a signal). The cycle is continued until all four dNTPs have been cycled through the device, after which the cycle is repeated. This cycling can be repeated until all the template DNA is exhausted, thus generating sequence data for the entire library of fragments.

Figure 17:
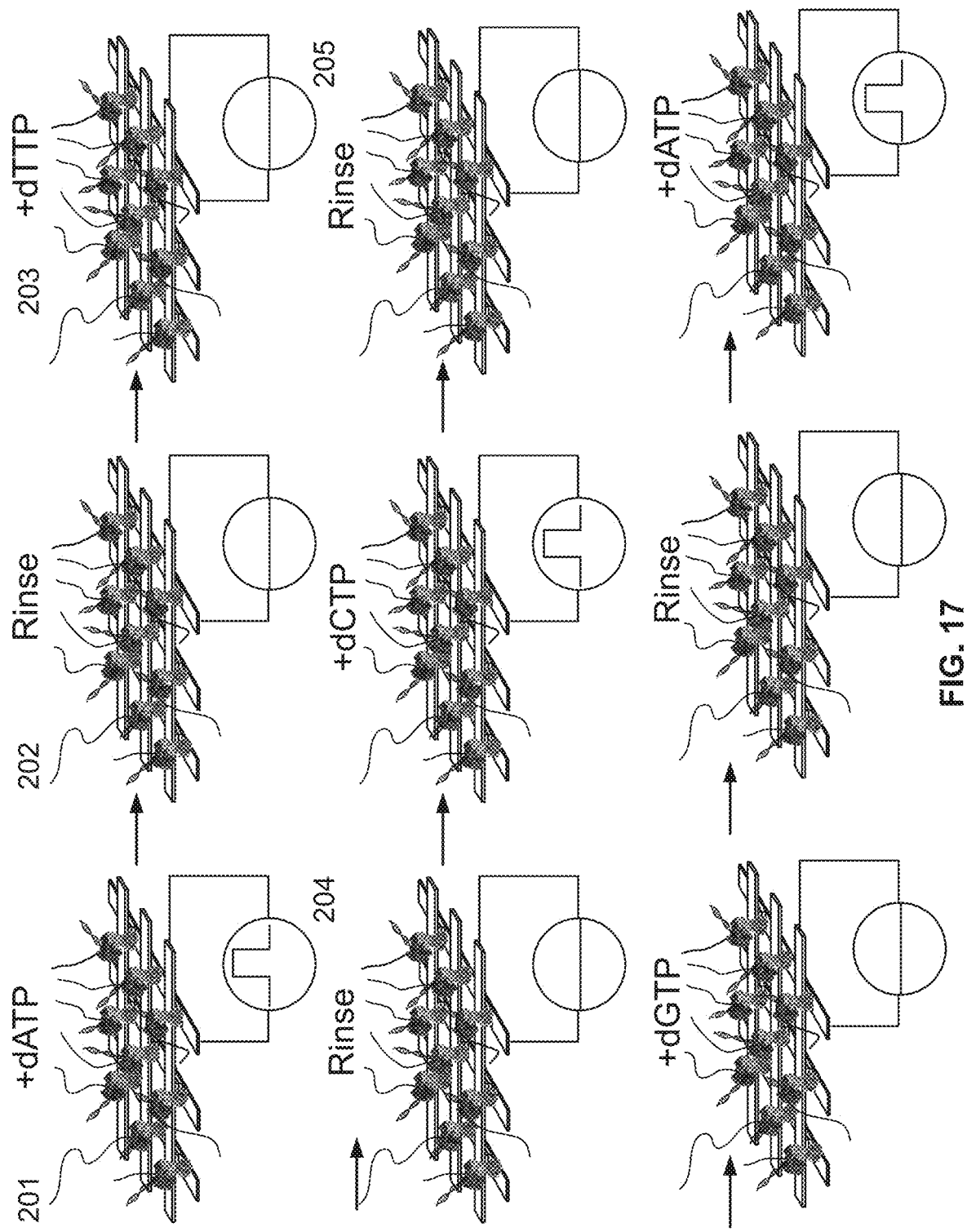
FIG. 17 shows a sequence of exposure to nucleotide triphosphates and rinses for determining the sequence of each template molecule at each site.

FIG. 17 shows a method for sequencing DNA. On adding dATP to the array 201, the molecule shown will generate a signal 204 as the A is incorporated into the extending chain. The array is then rinsed to remove dATP 202, and the next nucleotide (shown as dTTP here) added 203. The cycle is continued as shown. The addition of dATP, then dCTP and then dATP all give signals of base incorporation 204 whereas the presence of the other nucleotides do not 205. Accordingly, the sequence at that particular location will be recorded as TGT.

It will be recognized that this approach has two major advantages over current sequencing strategies that use cycling of dNTPs. One is that, by utilizing a single molecule read-out at a time-scale faster than the base-incorporation rate of a polymerase, it now becomes straightforward to count repeats of the same base. So the sequence AAAAA would give 5 distinct bursts of signal in the presence of dTTP, and so on. The second is that, in contrast to known optical readout schemes, the length of template that is read is not constrained by distance from the mounting substrate, so that the potential read length is as high as the processivity of the polymerase (10 kB for phi29).

Figure 18:
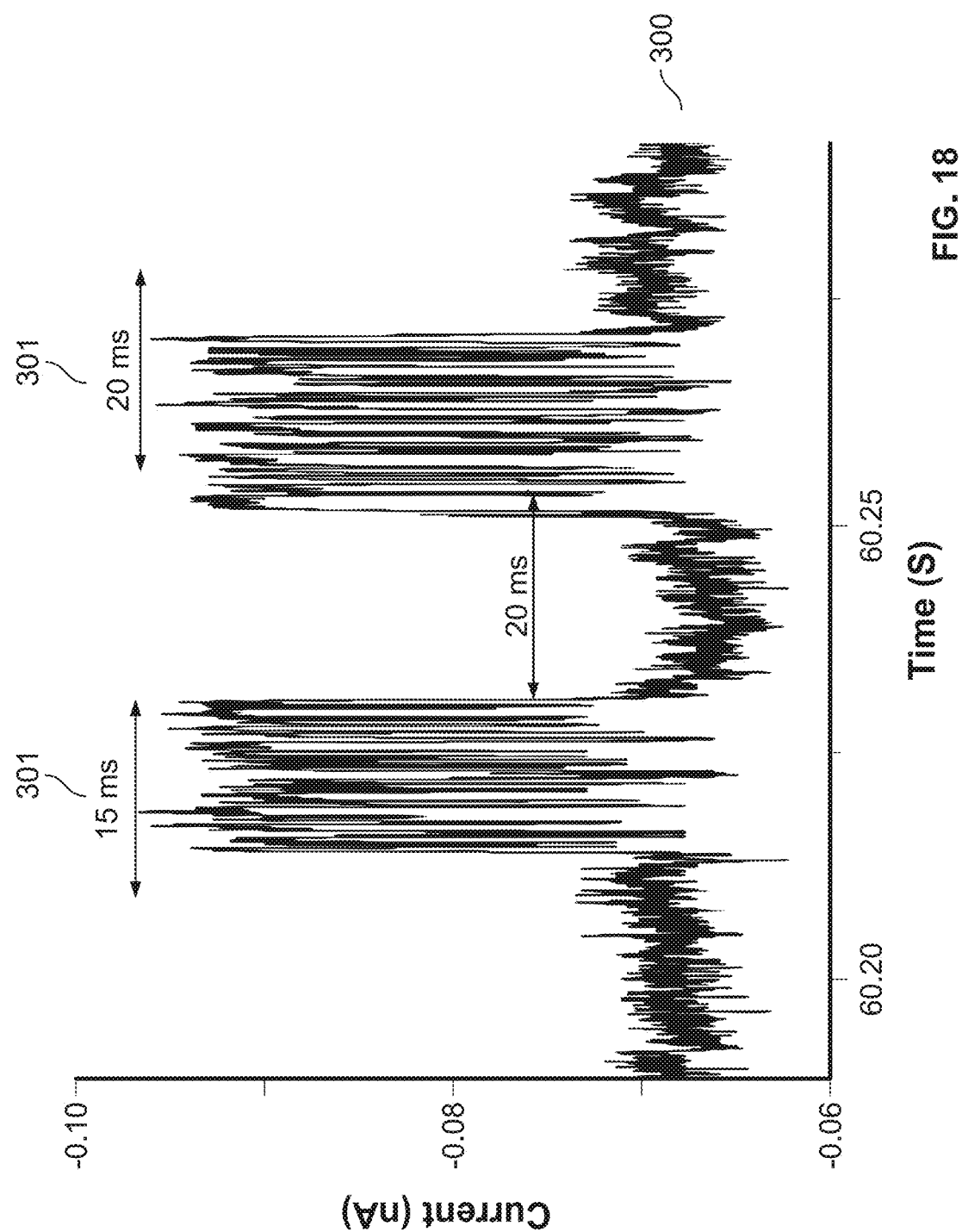
FIG. 18 shows two telegraph noise bursts characteristic of the sequential incorporation of two identical nucleotides at sites containing identical bases

FIG. 18 shows the ability to read individual sequential incorporations, and hence read homopolymeric runs of sequence. A current vs. time recording 300 shows the incorporation of two sequential bases (here, electrical data are shown for dTTP being incorporated at two successive A sites). Each signal consists of a burst 301 of telegraph noise of duration about 20 ms, separated by gaps between bursts, also, on average of about 10 to 20 ms at micromolar concentrations of nucleotide triphosphate. Thus, on any given step of the chemical cycling illustrated in FIG. 17, where just one nucleotide triphosphate is present, the number of repeated bases of its complement in the template strand may be counted simply by recording the number of such bursts of telegraph noise.

In another embodiment, the solution comprises more than one dNTP, with the dNTPs present in different concentrations. For example, the solution comprises 1 mM dATP, 100 µM dGTP 10 µM dCTP and 0.1 µM dTTP. In this embodiment, the polymerases in the array would generate signals continuously as each template is extended. At points where T is present in the template DNA, the signal of incorporation would follow the previous burst of telegraph noise rapidly (generally within 10 ms). The template DNAs in which the next base was a C would show a more delayed burst of telegraph noise because of the slower arrival of dGTP owing to its lower concentration. Similarly, templates containing a G would be preceded by a longer delay because of even lower concentration of dCTP. The longest delays would precede A bases because the concentration of dTTP is lowest.

In yet another embodiment, the two approaches can be combined, using 2 cycles of rinsing, using one pair of nucleotides in unequal concentration in the first cycle, and then the other two, also in unequal concentration in the second cycle.

While the preceding section describes methods of sequencing DNA using a system of arrays comprising a polymerase, the system of arrays can be easily modified to sequence other polymers as well.

Although the invention has been described and illustrated in the foregoing illustrative embodiments, it is understood that the present disclosure has been made only by way of example, and that numerous changes in the details of implementation of the invention can be made without departing from the spirit and scope of the invention. Features of the disclosed embodiments can be combined and rearranged in various ways. All publications, patents and other documents mentioned herein are incorporated by reference in their entirety.

REFERENCES

The following references are hereby incorporated by reference in their entireties:

Chen, Y.-S., C.-H. Lee, M.-Y. Hung, H.-A. Pan, J.-C. Chiou and G. S. Huang (2013). "DNA sequencing using electrical conductance measurements of a DNA polymerase." *Nature Nano Technology* 8: 452-458.

Choi, Y., I. S. Moody, P. C. Sims, S. R. Hunt, B. L. Corso, I. Perez, G. A. Weiss and P. G. Collins (2012). "Single-molecule lysozyme dynamics monitored by an electronic circuit." *Science* 335(6066): 319-324.

Merriman, B. and P. Mola, *Biomolecular Sensors and Methods*. US patent application number: WO 2016210386A1, 2016

Olsen, T. J., Y. Choi, P. C. Sims, O. T. Gul, B. L. Corso, C. Dong, W. A. Brown, P. G. Collins and G. A. Weiss (2013). "Electronic measurements of single-molecule processing by DNA polymerase I (Klenow fragment)." *J Am Chem Soc* 135(21): 7855-7860.

Zhang, B., W. Song, P. Pang, Y. Zhao, P. Zhang, I. Csabai, G. Vattay and S. Lindsay (2017). "Observation of Giant Conductance Fluctuations in a Protein." *Nano Futures* 1(3).

What is claimed is:

1. A device for direct measurement of protein activity, the device comprising:
   a first electrode and a second electrode, the first and second electrodes being separated by a gap; and
   a protein attached to the first electrode via a first linker and to the second electrode via a second linker, wherein each of the first and the second linkers comprises at least one chemical bond and is attached to a region of the protein that is inactive.

2. The device of claim 1, wherein the gap has a width of about 1.0 nm to about 20.0 nm.

3. The device of claim 1, wherein the first and second electrodes are separated by a dielectric layer, wherein a passivation layer is disposed on the first and second electrodes.

4. The device of claim 1, wherein the protein is selected from the group consisting of a polymerase, a nuclease, a proteasome, a glycopeptidase, a glycosidase, a kinase and an endonuclease.

5. The device of claim 1, wherein the protein is a polymerase.

6. The device of claim 5, wherein exonuclease activity of the polymerase is disabled.

7. The device of claim 1, wherein each of the first and second linkers comprises a covalent chemical bond.

8. The device of claim 1, wherein the protein is biotinylated.

9. The device of claim 1, wherein the first and/or the second linker comprises thiol-streptavidin.

10. The device of claim 1, wherein the protein and the first and/or second electrodes are biotinylated, and wherein the first and/or the second linker comprises a streptavidin molecule comprising at least two biotin binding sites.

11. The device of claim 1, wherein the first and/or second electrodes comprise a metal selected from the group consisting of gold, platinum, palladium, and ruthenium, or any combinations thereof.

12. The device of claim 1, wherein the first or the second linker is attached to the N-terminal region of the protein.

13. The device of claim 5, wherein the first or the second linker is attached to the exonuclease region of the polymerase.

14. A method for direct measurement of protein activity, the method comprising:
   (a) introducing a chemical entity that is capable of interacting with the protein of the device of claim 1;
   (b) applying a voltage bias between the first and second electrodes that is 100 mV or less; and
   (c) observing fluctuations in current between the first and second electrodes that occur when the chemical entity interacts with the protein.

15. A method of sequencing a biopolymer, said method comprising:
   (a) introducing a biopolymer to the device of claim 1;
   (b) applying a voltage bias between the first and second electrodes that is 100 mV or less;
   (c) detecting fluctuations in current between the first and second electrodes that occur when a monomer is removed from an end of the biopolymer; and
   (d) determining the identity of each monomer removed from the biopolymer.

16. The method of claim 15, wherein the biopolymer is a DNA molecule, an RNA molecule, a peptide, a polypeptide, or a glycan.

17. A method of sequencing a polynucleotide, said method comprising:
   (a) introducing a primed polynucleotide template to the device of claim 1, wherein the protein is a polymerase and wherein the polymerase is bound to the template;
   (b) introducing a solution comprising dNTPs;
   (c) applying a voltage bias between the first and second electrodes that is 100 mV or less;
   (d) detecting fluctuations in current between the first and second electrodes that occur when each dNTP is incorporated as an additional nucleotide complementary to a corresponding nucleotide in the polynucleotide template; and
   (e) determining the identity of each additional nucleotide being incorporated.

18. The method of claim 17, wherein each dNTP is present in the solution at about the same concentration.

19. The method of claim 17, wherein each dNTP is present at a concentration that is about equal to or above the saturation concentration of the template-bound polymerase.

20. The method of claim 17, wherein step (d) comprises detecting the presence of one or more current spike(s).

21. The method of claim 20, wherein step (e) comprises using the characteristics of each spike.

22. The method of claim 17, wherein each additional nucleotide is introduced in turn.

23. The method of claim 17, wherein each dNTP is introduced simultaneously, and wherein at least one dNTP is present at a lower concentration than that of the other dNTPs.

* * * * *

SEQUENCE LISTING

<160> NUMBER OF SEQ ID NOS: 6

<210> SEQ ID NO 1
<211> LENGTH: 17
<212> TYPE: PRT
<213> ORGANISM: Artificial Sequence
<220> FEATURE:
<223> OTHER INFORMATION: Synthetic peptide

<400> SEQUENCE: 1

Cys His Asn Thr Pro Val Tyr Lys Leu Asp Ile Ser Glu Ala Thr Gln
1               5                   10                  15

Val

<210> SEQ ID NO 2

-continued

```
<211> LENGTH: 12
<212> TYPE: PRT
<213> ORGANISM: Artificial Sequence
<220> FEATURE:
<223> OTHER INFORMATION: Synthetic peptide

<400> SEQUENCE: 2

Cys Ala Leu Asp Arg Trp Glu Lys Ile Arg Leu Arg
1               5                   10

<210> SEQ ID NO 3
<211> LENGTH: 38
<212> TYPE: PRT
<213> ORGANISM: Artificial Sequence
<220> FEATURE:
<223> OTHER INFORMATION: Synthetic peptide

<400> SEQUENCE: 3

Met Gly Ser Ser His His His His His His Ser Ser Gly Leu Val Pro
1               5                   10                  15

Arg Gly Ser Gly Leu Asn Asp Ile Phe Glu Ala Gln Lys Ile Glu Trp
            20                  25                  30

His Glu Gly Ala Ser Ser
        35

<210> SEQ ID NO 4
<211> LENGTH: 15
<212> TYPE: PRT
<213> ORGANISM: Artificial Sequence
<220> FEATURE:
<223> OTHER INFORMATION: Synthetic peptide

<400> SEQUENCE: 4

Gly Leu Asn Asp Ile Phe Glu Ala Gln Lys Ile Glu Trp His Glu
1               5                   10                  15

<210> SEQ ID NO 5
<211> LENGTH: 84
<212> TYPE: PRT
<213> ORGANISM: Artificial Sequence
<220> FEATURE:
<223> OTHER INFORMATION: Synthetic peptide

<400> SEQUENCE: 5

Cys Gly Ser Ser His His His His His His Ser Ser Phe Thr Leu Ile
1               5                   10                  15

Glu Leu Leu Ile Val Val Ala Ile Ile Gly Ile Leu Ala Ala Ile Ala
            20                  25                  30

Ile Pro Gln Phe Ser Ala Tyr Arg Val Lys Ala Tyr Asn Ser Ala Ala
        35                  40                  45

Ser Ser Asp Arg Leu Asn Leu Lys Thr Ala Leu Glu Ser Ala Phe Ala
    50                  55                  60

Asp Asp Gln Thr Tyr Pro Pro Glu Ser Gly Leu Val Pro Arg Gly Ser
65                  70                  75                  80

Gly Ala Ser Ser

<210> SEQ ID NO 6
<211> LENGTH: 64
<212> TYPE: PRT
<213> ORGANISM: Artificial Sequence
<220> FEATURE:
<223> OTHER INFORMATION: Synthetic peptide

<400> SEQUENCE: 6
```

```
Ala Ala Phe Thr Leu Ile Glu Leu Leu Ile Val Val Ala Ile Ile Gly
1               5                   10                  15

Ile Leu Ala Ala Ile Ala Ile Pro Gln Phe Ser Ala Tyr Arg Val Lys
                20              25                  30

Ala Tyr Asn Ser Ala Ala Ser Ser Asp Arg Leu Asn Leu Lys Thr Ala
        35              40                  45

Leu Glu Ser Ala Phe Ala Asp Asp Gln Thr Tyr Pro Pro Glu Ser Cys
    50              55              60
```

UNITED STATES PATENT AND TRADEMARK OFFICE
CERTIFICATE OF CORRECTION

| | |
|---|---|
| PATENT NO. | : 11,808,755 B2 |
| APPLICATION NO. | : 17/055771 |
| DATED | : November 7, 2023 |
| INVENTOR(S) | : Lindsey et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 107 days.

Signed and Sealed this
First Day of July, 2025

Coke Morgan Stewart
*Acting Director of the United States Patent and Trademark Office*